(12) United States Patent
Schwartz et al.

(10) Patent No.: US 11,179,479 B2
(45) Date of Patent: **\*Nov. 23, 2021**

(54) ENHANCED CARDIOMYOCYTE REGENERATION

(71) Applicant: Animatus Biosciences, LLC, Houston, TX (US)

(72) Inventors: Robert Schwartz, Houston, TX (US); Dinakar Iyer, Houston, TX (US); Siyu Xiao, Houston, TX (US)

(73) Assignee: ANIMATUS BIOSCIENCES, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/115,698

(22) Filed: Dec. 8, 2020

(65) Prior Publication Data

US 2021/0187123 A1    Jun. 24, 2021

Related U.S. Application Data

(63) Continuation-in-part of application No. 16/959,944, filed as application No. PCT/US2018/068203 on Dec. 31, 2018.

(60) Provisional application No. 62/945,513, filed on Dec. 9, 2019, provisional application No. 62/614,190, filed on Jan. 5, 2018.

(51) Int. Cl.
*C12N 15/88* (2006.01)
*A61K 9/10* (2006.01)
*A61K 48/00* (2006.01)
*C12N 5/077* (2010.01)
*A61P 9/10* (2006.01)
*A61P 9/04* (2006.01)

(52) U.S. Cl.
CPC ........ *A61K 48/005* (2013.01); *A61K 48/0075* (2013.01); *A61P 9/04* (2018.01); *A61P 9/10* (2018.01); *C12N 5/0657* (2013.01); *C12N 15/88* (2013.01); *C12N 2510/00* (2013.01)

(58) Field of Classification Search
CPC .................................................. A61K 48/005
See application file for complete search history.

(56) References Cited

U.S. PATENT DOCUMENTS

| 7,811,820 B2 * | 10/2010 | Schwartz ........... A61K 38/1709 435/377 |
| 10,590,419 B2 | 3/2020 | Morrisey |
| 2019/0175690 A1 | 6/2019 | Pu et al. |

FOREIGN PATENT DOCUMENTS

| WO | 20180170172 A1 | 9/2018 | |
| WO | 2019136031 A1 | 7/2019 | |
| WO | WO 2011/011767 | * 1/2020 | ............. C12N 15/87 |

* cited by examiner

*Primary Examiner* — Christopher M Babic
*Assistant Examiner* — Alexander W Nicol
(74) *Attorney, Agent, or Firm* — Eric P. Mirabel; Elizabeth Hall

(57) ABSTRACT

Compositions and methods for promoting adult mammalian cardiomyocytes processes and systems for enhancing cardiomyocyte regeneration are described. The invention relates to locally administering a therapeutic agent containing a modified messenger RNA for expressing a mutated serum response factor polypeptide and a modified messenger RNA for expressing a mutated YAP polypeptide into diseased heart muscle to promote cardiomyocyte proliferation and cardiac regeneration.

22 Claims, 11 Drawing Sheets

Specification includes a Sequence Listing.

Cardiomyocyte Differentiation

Cardiomyocyte proliferation

ENHANCED CARDIOMYOCYTE REGENERATION

CROSS REFERENCE TO RELATED APPLICATIONS

This application is a continuation in part and claims priority to pending U.S. application Ser. No. 16/959,944 filed on Jul. 2, 2020 a US National Stage Entry of PCT/US2018/068203 filed Dec. 31, 2018. This application also claims priority to U.S. Provisional Patent Application Ser. No. 62/945,513, filed Dec. 9, 2019 entitled "Enhanced Cardiomycyte De-Differentiation." The entire contents of these applications are hereby incorporated herein by reference.

INCORPORATION BY REFERENCE

This application includes a sequence listing in computer readable form (a "txt" file) that is submitted herewith on ASCII text file named SeqList031421.txt, created on Mar. 14, 2021 and 24,257 bytes in size. This sequence listing is incorporated by reference herein.

FIELD OF INVENTION

The present invention relates generally to compositions and methods for promoting adult mammalian cardiomyocytes processes and systems for enhancing cardiomyocyte regeneration. More specifically, the invention relates to locally administering a therapeutic agent containing a modified messenger RNA for expressing a mutated serum response factor polypeptide and a modified messenger RNA for expressing a mutated YAP polypeptide into diseased heart muscle to promote its regeneration.

BACKGROUND OF THE INVENTION

Throughout the history of modern medicine the adult human heart has been considered a terminally differentiated organ with extremely limited capacity to regenerate after injury. Diseases of the heart are the most serious public health problem facing the United States and the developing world and the loss of cardiomyocytes underlies most causes of heart failure.

The current standard treatment for extensive heart failure is heart transplantation, but the limited availability of donor hearts and the risk of rejection limit its widespread use. The use of stem cells to repair damaged myocardium has also been proposed. It has been shown that different stem cell types from which cardiomyocytes (CMs) can be derived include embryonic stem cells (ESC), Induced Pluripotent Stem Cells (iPSCs), bone marrow derived mesenchymal stem cells and Cardiac Progenitor Cells (CPCs) from adult cardiac tissue. However, developing therapies with these cell types has presented multiple problems including ethical issues, potential teratoma formation, and the need for immunosuppression.

There is a long standing need for a different approach to improve the treatment options and repair processes needed to deal with heart disease.

SUMMARY OF THE INVENTION

The present invention relates generally to compositions and methods for promoting adult mammalian cardiomyocytes processes and systems for enhancing cardiomyocyte regeneration. More specifically, the invention relates to locally administering a therapeutic agent containing a modified messenger RNA for expressing a mutated serum response factor polypeptide and a modified messenger RNA for expressing a mutated YAP polypeptide into diseased heart muscle to promote its regeneration.

One embodiment of the invention is a composition used to enhance cardiomyocyte regeneration. The composition, used in the treatment of heart disease, includes: a) a first modified messenger RNA for expressing a mutated serum response factor polypeptide; b) a second modified messenger RNA for expressing a mutated YAP polypeptide; and c) a delivery agent for delivering the first and second modified messenger RNAs into a cell.

The mutated serum response factor polypeptide in the composition is generally selected from SRF-141(A3), SRF-144(A3), SRF-147(A3), SRF-150(A3), SRF-153(A3), or combinations thereof. The mutated YAP polypeptide in the composition is preferably YAP1(5SA). The delivery agent used for the composition is either a viral transduction vector or a liposomal transfection agent.

Another embodiment of the invention is a method of inducing cardiomyocyte regeneration comprising: a) preparing a first modified messenger RNA for expressing a mutated serum response factor polypeptide; b) preparing a second modified messenger RNA for expressing a mutated YAP polypeptide; c) delivering the first and second modified messenger RNAs using a delivery agent into a cardiomyocyte.

Yet Another embodiment of the invention is a method for promoting cardiac repair and regeneration in a subject, the method comprising injecting an effective amount of a therapeutic composition into a site of a heart of the subject, wherein the composition comprises a first modified messenger RNA for expressing a mutated serum response factor polypeptide, a second modified messenger RNA for expressing a mutated YAP polypeptide, and a delivery agent for delivering the first and second modified messenger RNAs into a cardiomyocyte.

Another embodiment of the invention is a method for promoting cardiac repair and regeneration in a subject, the method comprising identifying a site of cardiac muscle damage in a heart of the subject and injecting a therapeutic composition into the heart adjacent the site of cardiac muscle damage. Typically, multiple injections of the therapeutic composition are made at different locations in the heart wherein each injection location is adjacent to an identified site of cardiac damage.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the compositions or methods for carrying out the same purposes as those described herein.

DETAILED DESCRIPTION OF ILLUSTRATIVE EMBODIMENTS

Figure 1A:
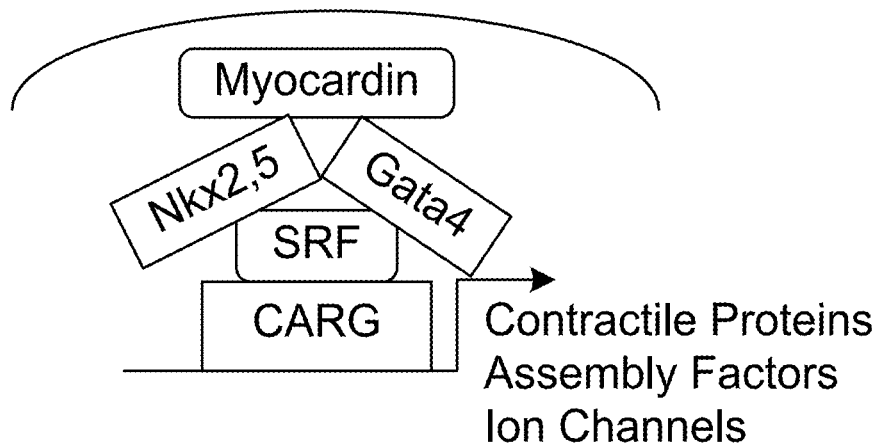
FIGS. 1A and 1B schematically illustrate the role of the CArG box recruitment of serum response factor and its interaction with various co-factors in cardiomyocyte differentiation and proliferation.

While the specification concludes with the claims particularly pointing and distinctly claiming the invention, it is believed that the present invention will be better understood from the following description. The present invention can comprise the components of the present invention as well as other ingredients or elements described herein. As used herein, "comprising" means the elements recited, or their equivalent, plus any other element or elements which are not recited. The terms "having," "including," and "comprised of" are also to be construed as open ended unless the context suggests otherwise.

The term "about", as used herein, refers to a +/−10% variation from the nominal value. It is to be understood that such a variation is always included in a given value provided herein, whether or not it is specifically referred to. All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skilled in the art. This includes, at the very least, the degree of expected experimental error, technique error and instrument error for a given technique used to measure a value.

The term "effective amount", as used herein, refers to an amount of a composition or compound that is capable of producing a medically desirable result in a treated subject. The medically desirable result may be objective (i.e., measurable by some test or marker) or subjective (i.e., subject gives an indication of or feels an effect).

The term "subject", as used herein, refers to a mammal including a human in need of therapy for, or susceptible to, a condition or its sequelae. The subject may include humans, dogs, cats, pigs, cows, sheep, horses, goats, rats, and mice, hamsters, and guinea pigs. The term "subject" does not exclude an individual that is normal in all measurements made. A subject may be identified in the judgment.

The term "treatment", as used herein, may refer to the administration of a substance or composition to a subject with the purpose to cure, alleviate, relieve, remedy, prevent, suppress, inhibit, or ameliorate a disorder, symptoms of the disorder, a disease state secondary to the disorder, or a predisposition toward the disorder. "Treating" may refer to a therapeutic treatment or prophylactic or preventative measures, wherein the object is to prevent or lessen the targeted pathologic condition or disorder as described hereinabove, or "treating" may refer only to therapeutic treatment. Thus, "treating" may include directly affecting or curing, suppressing, inhibiting, preventing, reducing the severity of, delaying the onset of, reducing symptoms associated with the disease, disorder or condition, or a combination thereof. Additionally, "treating" refers inter alia to delaying progression, expediting remission, inducing remission, augmenting remission, speeding recovery, increasing efficacy of, or decreasing resistance to alternative therapeutics, or a combination thereof.

The present invention relates to compositions and methods for promoting adult mammalian cardiomyocyte processes and systems for enhancing cardiomyocyte regeneration are described. The invention relates to locally administering a therapeutic agent containing a modified messenger RNA for expressing a mutated serum response factor polypeptide and a modified messenger RNA for expressing a mutated YAP polypeptide into diseased heart muscle to promote cardiomyocyte proliferation and cardiac regeneration.

Heart development (also known as cardiogenesis) refers to the prenatal development of the heart. The heart is the first functional organ in vertebrate embryos and beats spontaneously by week 4 of development. Although there is some evidence for a very low level of postnatal cardiomyocyte proliferation which can be increased after injury in mice, it is insufficient to replenish lost cardiomyocytes that are damaged or to re-establish proper heart function. Even that level of postnatal cardiomyocyte proliferation in mice is lost seven days after birth. Not only does cardiomyocyte cell division slow down after birth, but it responds to physiological or pathological challenges thereafter through cardiac hypertrophy (Fan et al., 2015).

This loss of proliferative response corresponds to the exit of cardiomyocytes from the cell cycle and demonstrates that adult mammalian cardiomyocytes are refractory to mitotic activity, unlike those found in either early postnatal mice or zebrafish.

One important hurdle for cardiomyocytes to overcome in re-entering the cell cycle is the rigidity of the sarcomere structure which is the basic contractile unit of muscle fiber. The sarcomeres must be disassembled for cytokinesis to occur (Sanger, et al., 2010) Such disassembly may require signals for cardiomyocyte de-differentiation, which is accompanied by multiple cellular changes including reactivation of gene expression programs restricted to the embryonic state.

Therefore the major question regarding vertebrate heart development is how transcription factors broadly expressed in the embryo regulate cardiomyocyte differentiation and proliferation. By understanding the expression patterns of genes involved in cardiac muscle differentiation, it might be possible to reverse the senescent process in adult myocytes by enabling them to re-enter and exit the cell cycle and thus repair the heart with a neo-cardiomyocyte population.

Fetal cardiomyocytes proliferate in two consecutive steps. First, sarcomeres must be disassembled to enable chromosome segregation to complete the cell division cycle because the sarcomere occupies a large volume of the mature cardiomyocyte that physically impedes mitosis and cytokinesis. Thus, sarcomere disassembly is a prerequisite task for cardiomyocyte proliferation. Once disassembly is achieved myocyte replication can proceed. Next, the sarcomeres must reassemble after cell division to form its contractile apparatus so that the cells regain the function to contract. Thus, regulatory factors involved in sarcomeres assembly and disassembly are critical for cardiomyocyte proliferation.

Serum Response Factor (SRF)

Human serum response factor, also known as SRF, is a well known protein whose sequence is given as SEQ ID NO: 1. SRF is a member of an ancient DNA binding protein family that shares a highly conserved DNA-binding/dimerization domain of 90 amino acids termed the MADS (MCM1, Agamous, Deficiens, and SRF) box superfamily of transcription factors (Treisman, 1994; Reecy et al., 1999; Miano, 2003). SRF binds to the serum response element (SRE) in the promoter region of target genes. SRF is known to regulate the activity of many early genes, such as c-fos, whereby it participates in cell cycle regulation, apoptosis, cell growth, and cell differentiation. This gene is the downstream target of many pathways; for example, the mitogen-activated protein kinase pathway (MAPK) that acts through the ternary complex factors (TCFs).

Figure 1B:
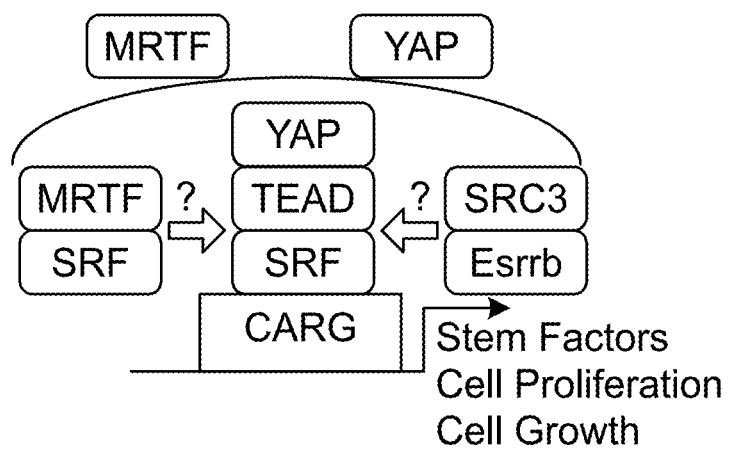

MADS boxes have similar DNA binding specificities and dimerize to symmetrically contact the serum response element (SRE) with a consensus sequence CC(A/T)$_6$GG, also known as the SRE and or the CArG box. As illustrated in FIGS. 1A and 1B, SRF interaction with cofactors has a regulatory role in both the differentiation and proliferation of cardiomyocytes.

The appearance and diversification of nascent embryonic cardiac and smooth muscle cells require the combinatorial interactions of SRF with other transcription factors enriched in early progenitor cells. In fact, a large number of cardiac and virtually all of the smooth muscle-expressed genes to date are dependent upon CArG boxes. Mutations that prevent SRF binding severely impair the expression of c-fos, as well as muscle restricted genes (Shore and Sharrocks, 1994; Chen and Schwartz, 1996).

CArG boxes recruit SRF and SRF cofactors (such as Nkx2.5, and GATA4) that strongly enhance SRF-DNA binding affinity, thus permitting the formation of higher order DNA binding complexes at relatively low SRF levels (Chen and Schwartz, 1996; Sepulveda et al., 2002). Similarly, CArG boxes recruit the cysteine-rich protein 2 LEVI, which bridges the SRF and GATA factors through interaction with the MADS N-terminal extension (Sepulveda et al., 2002) and myocardin, which competes with Erythroblast Transformation Specific (ETS) factors, the ERS family of transcription factors, that interact with the loop region of the MADS box (Wang et al., 2002; Wang et al., 2004). Mutations of the SRF MADS box prevent SRF binding and severely impair the expression of c-fos, as well as muscle-restricted genes (note the interaction of these factors in cardiomyocyte differentiation in the proposed model of SRF interactome with co-factors shown in FIG. 1A).

An aspartic acid substitution at Ser162 of SRF MADS box blocked SRF-DNA binding and α-actin gene transcription, but allowed for ETS factor dependent cell replication through binding of ternary complex factors (TCFs). Other mediators of cell signaling through SRF are the myocardin related transcription factors (MRTFs). The effect of RhoA on SRF dependent genes is mediated through a TCF independent mechanism (Hill and Treisman, 1995). The myocardin family proteins MRTF-AB provide the link between RhoA-dependent cytoskeletal regulation and SRF-dependent gene expression (Lockman et al., 2004; Miralles et al., 2003; Wang et al., 2002). Mechanistically, MRTF-A associates with G-actin and is thus sequestrated in the cytoplasm under resting conditions. Signals such as serum stimulation activate RhoA to promote actin polymerization, therefore leading to MRTF-A dissociating from G-actin, whereupon it translocates into the nucleus and triggers activation of SRF targets (Yu et al., 2015).

TEAD associates with MRTF-A overlapping the myocardin binding site on the SRF's MADS box, thus it facilitates signaling through actin tread milling leading to Rho kinase activation and cell replication (Zaromytidou et al., 2006). The recruitment of YAP, TEAD, and other co-factors such as NCOA3/SRC3 and ESRRB may propel the cells further towards cell survival and activate stem factor activity. For example, SRC3 is an essential coactivator required to mediate ESRRB function in embryonic stem cells. SRC3 interacts with ESRRB via its ligand-binding domain and bridges ESRRB to RNA polymerase II complexes (Percharde et al., 2012). Functionally, SRC3 is critical for both the induction and maintenance of pluripotency and cell replication. Thus, the association between SRC3, ESRRB, TEAD, YAP, and SRF may be important in promoting cardiomyocyte proliferation as shown in FIG. 1B. FIGS. 1A and 1B illustrate the potential competition between transcription factors that facilitate proliferation versus cardiomyocyte differentiation through interactomes with the SRF MADS box.

All of these myogenic cofactors greatly enhance SRF transactivation. Thus, the MADS box domain has been proposed to be an important regulatory nexus for the convergence of crucial cellular signals enabling SRF to recruit specific cofactors to their respective DNA binding sites and enhance transactivation of target genes. For example, SRF has a core domain of 90 amino acids required for dimerization and sequence specific DNA binding (Sharrocks, 1995; Treisman, 1995). The highly conserved MADS box within this core domain is necessary for critical interactions with co-accessory factors (Pellegrini, 1995). Furthermore, all DNA contacts occur within the N-terminal portion of the MADS box, and SRF-SRF dimerization is mediated by elements within the MADS box together with additional residues from the immediately adjacent C terminal region (Pellegrini, 1995). Hence a comprehensive dissection of the SRF core domain and especially of the MADS box is essential for understanding how SRF regulates cardiomyogenesis. All of these myogenic cofactors greatly enhance SRF's activation of its targets. For example, SRF activity controls sarcomerogenesis in higher vertebrate and supports the concept that SRF resides at a high point in the regulator hierarchy governing sarcomerogenesis (Niu, et al., 2005; Niu, et al., 2008). One SRF mutant named Stemin (SEQ ID NO: 2) has been shown to block the normal SRF-mediated cardiac muscle differentiation program resulting in the production of undifferentiated cardiomyocytes. Thus, the MADS box domain is likely to be an important regulatory nexus for the convergence of crucial cellular signals enabling SRF to recruit specific cofactors to their respective DNA binding sites and enhance transactivation of target genes.

An important SRF sequence (SEQ ID NO: 4), sometimes referred to as the SRF core domain, is shown below with the MADS box in bolded letters.

```
132-SGAKPGKKTRGRVKIKMEFIDNKLRRYT
      N-terminal extension

TFSKRKTGIMKKAYELSTLT-179
αI coil

180-GTQVLLLVASETGHVYTFTRKLQPMITS
      βI coil β-loop βII coil

ETGKALIQTCLNSPD-223
     αII coil
```

The MADS box is a region for interactions with critical transcription regulating co-accessory factors. There are likely to be distinct sites for interactions with cofactors that regulate the transcription of proliferation genes and others for interactions with cofactors that regulate the transcription of differentiation genes. For example, one key site that modulates SRF's transcriptional activity towards proliferation genes is well known. That site includes a region in the βII coil of the MADS box (aa 194-198) that binds to the Ets protein Elk1 to form a ternary complex with SRF and the c-fos promoter, leading to increased transcription.

YAP and the HIPPO Pathway

The Hippo pathway is a highly conserved signaling pathway in mammals that is thought to control organ size during the developmental processes by regulating cell proliferation and cell apoptosis (Zhao et al., 2010). It has also been suggested that the Hippo pathway may regulate cell self-renewal and expansion.

Mechanistically, Yes-associated protein (YAP), a transcription co-activator and a potent growth promoter, is directly phosphorylated by the Hippo pathway kinases Lats1 and Lats2, and then inhibited through cytoplasmic retention and degradation. Chemical and physical signals such as GPCR ligands and matrix stiffness dampen the Hippo pathway, thus leading to YAP activation, which facilitates cell proliferation, evasion from apoptosis, and stem cell self-renewal. Additional studies have indicated that the Hippo pathway is upregulated in heart failure and that a Hippo pathway deficiency reversed systolic heart failure (Leach et al., 2017). Such results have increased interest in the manipulation of the Hippo pathway as an approach to the treatment of heart failure.

Human YAP1 (NM 0130145.3.trans 1; 403-1917) is important is a central player in a cascade of phosphorylation events in the Hippo pathway. The phosphorylation of YAP1 prevents shuttling of YAP1 into the nucleus, promotes 14-3-3 binding, and protein degradation. When the Hippo pathway is inactivated, unphosphorylated YAP1 enters the nucleus and binds to multiple transcription factors (e.g. TEAD/TEF and MRTFa). YAP1 binding to its partners in the nucleus, typically promotes gene expression programs that favor cell survival, proliferation, and tissue growth (Xiao, et al., 2016; Ikeda & Sadoshina, 2016).

In the mammalian Hippo signaling pathway, MST1 (Mammalian STE20-like protein kinase 1), MST2, and SAV1 (Salvador homologue 1) form a complex to phosphorylate and activate LATS1 (Large tumor suppressor homologue 1) and LATS2 (Large tumor suppressor homologue 2). LATS1 and LATS2 then interact with MOB1A (MOB domain kinase activator 1A) and MOB1B (MOB domain kinase activator 1B), which further phosphorylate the downstream effectors including YAP (Yes-associated protein) and TAZ (Transcriptional co-activator with PDZ-binding motif). Transcription co-activators YAP and TAZ are the key regulators in the Hippo pathway regulated by cell proliferation and cell adhesion through phosphorylation. Activation of the Hippo signaling pathway inhibits YAP and TAZ transcriptional activity by promoting their degradation through phosphorylation, therefore preventing their translocation into the nucleus. When the Hippo signaling pathway is inactivated, TEADs (TEA domain transcription factor family members) serve as the main binding platforms of YAP and TAZ to bind to nuclear targets.

Because of the role of the Hippo signaling pathway in cell proliferation and organ size control, manipulating the Hippo pathway may be a potential strategy for promoting cardiac cell proliferation and cardiac regeneration. YAP and TAZ have been reported to control TBXS-dependent transcription, thus involved in cardiac and limb development. Mice with Sav1 conditional knockout in the heart showed expanded ventricular myocardial layers without expansion in cardiomyocyte size.

Thus, the transcription co-activator YAP, as a key regulator in the Hippo signaling pathway, has been proposed as a target for manipulation. Zhao et al. generated an active form of YAP, termed YAP5SA, by mutating all the LATS1/2 phosphorylation sites from serine to alanine (Zhao et al., 2007). The phosphorylation sites mutation of YAP prevents 14-3-3 binding, thus preventing YAP protein degradation. YAP5SA enters nucleus and binds with TEAD to regulate nuclear targets. Recently, YAP5SA has been proven to partially reprogram the highly differentiated adult mouse cardiomyocytes to a more primitive proliferative state (Monroe et al., 2019).

SRF Mutants

Figure 2A:
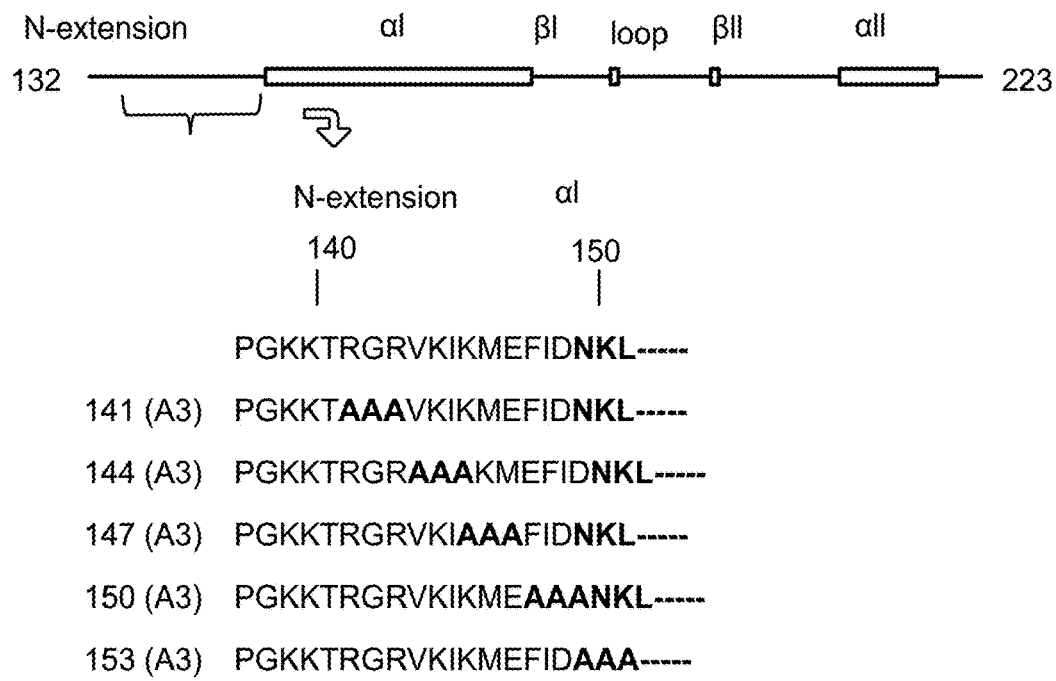
FIG. 2A illustrates several triplet alanine scanning mutations across the MADS box of SRF that were made and tested. The uppermost sequence is amino acid nos. 5 to 24 of SEQ ID NO:5. The next sequence labeled as 141(A3) is amino acid nos. 5 to 24 of SEQ ID NO:8. The next sequence labeled as 144(A3) is amino acid nos. 5 to 24 of SEQ ID NO:9. The next sequence labeled as 147(A3) is amino acid nos. 5 to 24 of SEQ ID NO:7. The next sequence labeled as 150(A3) is amino acid nos. 5 to 24 of SEQ ID NO:10. The last sequence labeled as 153(A3) is amino acid nos. 5 to 24 of SEQ ID NO:6.

Mutated polypeptides, including all or at least 22 residues of the sequence within the residues 132-179 (SEQ ID NO: 5) in the MADS box of the SRF core domain sequence (SEQ ID NO: 4). Of particular interest were molecules containing one or more mutations that block Nkx2.5 and/or GATA4 interactions, where the mutations are within the residues 132-179 (N-terminus through the alpha 1 domain 179 aa of the MADS box). These SRF mutants include mutations that insert, remove or change one or more residues within this same region that stimulate a stem cell factor, such as Nanog and Oct4. For example, the mutations may be substitutions of residues 147 and/or 153, deletions of residues 147 and/or 153, and one to three residue insertions adjacent to or within 2-3 residues of residues 147 and/or 153 incorporating triplet alanine scanning mutations across the MADS box of SRF (see FIG. 2) were made and tested to determine if they interfered with the association of these co-accessory factors. These mutants are referred to herein according to where the alanine triplet was placed within residues 132-179 (SEQ ID NO: 5) such as SRF-141(A3) (SEQ ID NO: 8), SRF-144 (A3) (SEQ ID NO: 9), SRF-147(A3) (SEQ ID NO: 7), SRF-150(A3) (SEQ ID NO: 10), or SRF-153(A3) (SEQ ID NO: 6).

Figure 2B:
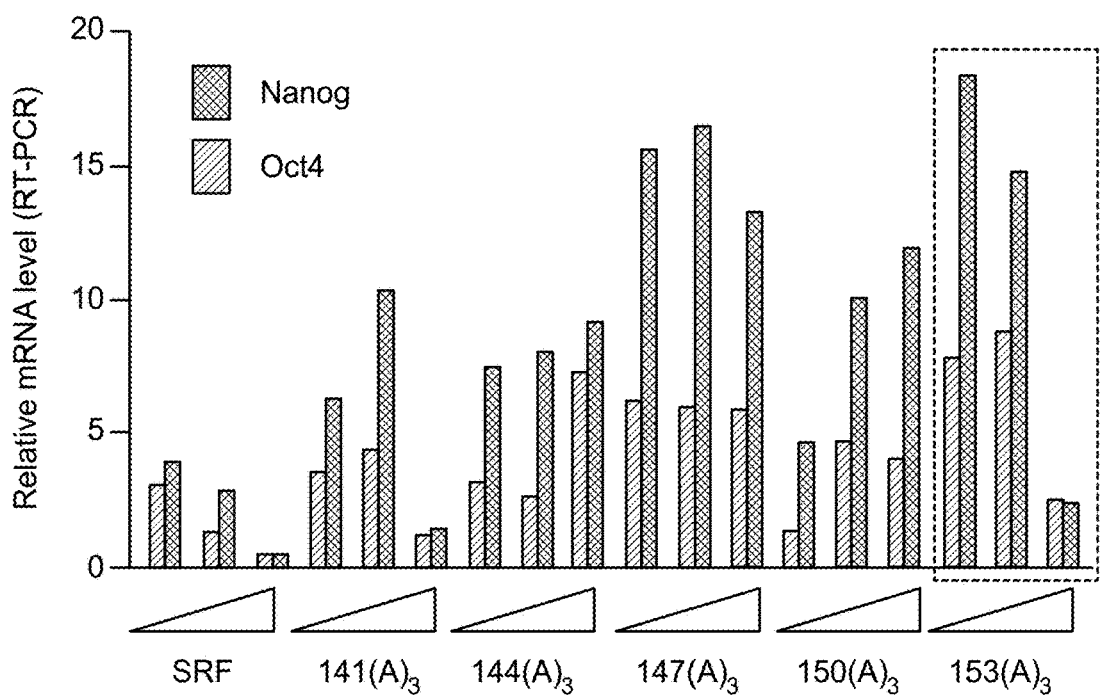
FIG. 2B illustrates the stimulation of the stem cell factors Nanog and Oct4 in cardiomycytes in response to the polypeptide mutations shown in FIG. 2A.

SRF's cooperative interactions with Nkx2.5 and GATA4 mapped to the N-extension of the MADS box and were blocked by several of the SRF triple alanine mutants as shown by the inhibition of the cardiac actin promoterluciferase reporter. Surprisingly, virtually every SRF mutation within the residues 132-179 (SEQ ID NO: 5) in the MADS box of the SRF core domain caused an increase in Nanog and Oct4 gene expression, with the strongest induction elicited by mutants SRF-147(A3) (SEQ ID 3) and SRF-153(A3) (SEQ ID 2) as shown in FIG. 2B. The applicants therefore contemplate the generation of different mutations, i.e. insertions (single, double or triple), deletions and substitutions (conservative or non-conservative) of the region of residues 147-153 of SRF.

Figure 4:
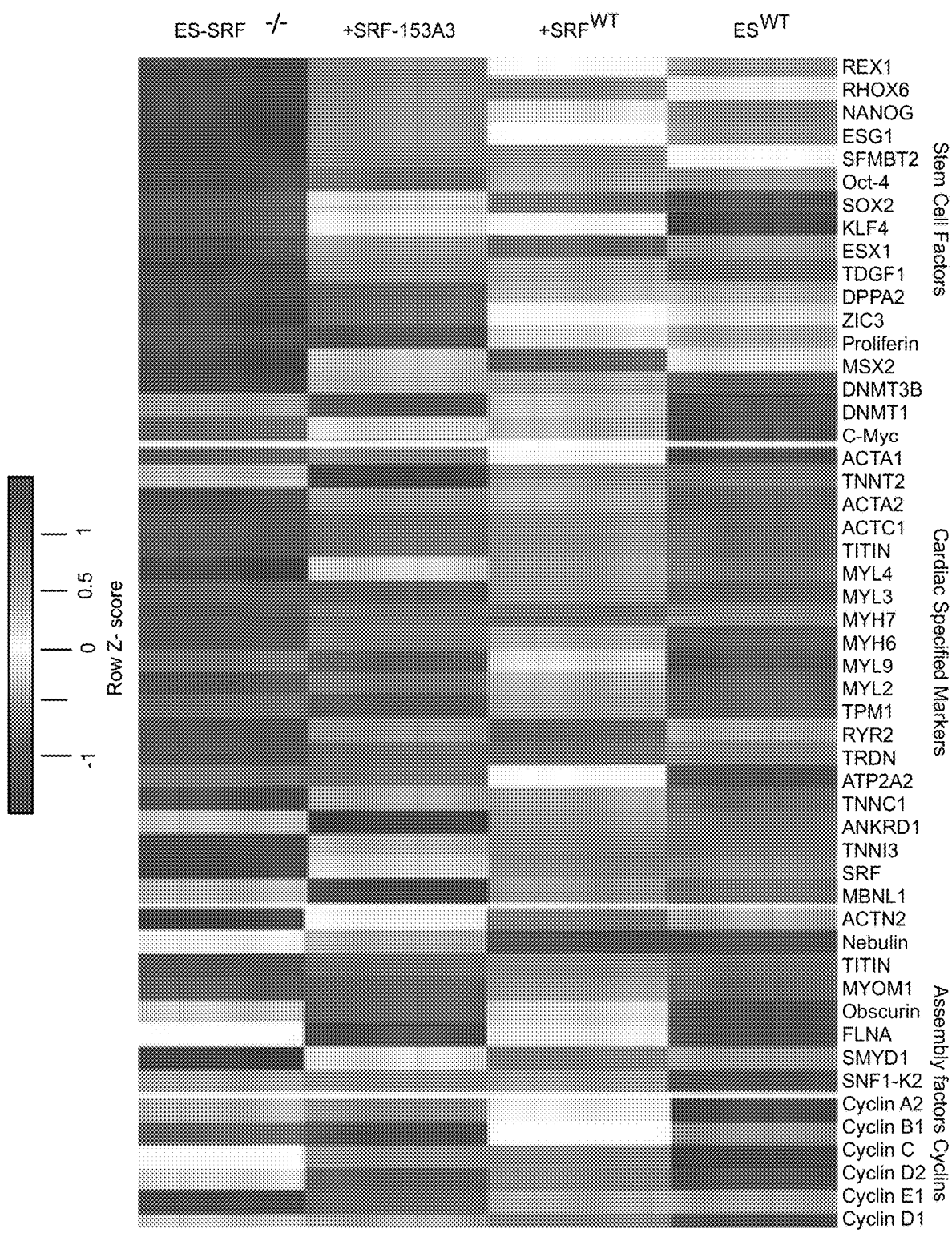
FIG. 4 shows that SRF153 mutant (Stemin) induced stem cell factors, blocked contractile proteins and assembly factors and activated cyclins.

For example, a study involving one SRF mutant (SRF-153(A3), referred to herein as Stemin (SEQ ID 2), showed that Stemin inhibited the induction of sarcomere assembly factors involved in cardiomyocyte differentiation thereby blocking the normal SRF-mediated cardiac muscle differentiation program resulting in the production of undifferentiated, proliferative cells (see FIG. 4). For example Stemin, or SRF-153(A3), showed a powerful activation of at least 15 stem cell marker genes, such as Rex1, Nanog, Oct4, Sox2, Esg1, SFmbt2, Rhox6 and proliferin, but not C-Myc and Klf4 in comparison to SRF null embryonic stem cells (ES cells). Thus, Stemin elicited an imperfect or partial pluripotency program. Stemin also inhibited the induction of many cardiac myocyte specified genes such as sarcomeric actins, heavy and light chain myosins, troponins, channels and structural genes. Expression of sarcomeric assembly factors such as Actinin2, Nebulin, Titin, Myomesin, Obscurin Filamin, Smyd1 and SNF1-K2 were blocked from appearing in comparison to wild type ES cells that formed cardiac myocytes following hanging drop formation. In addition, evidence for Stemin fostering cell replication was shown by the up regulation of cyclins A2, B 1, E1 and D1. The applicants' observation that a single transcription factor, Stemin, albeit mutated SRF, induced the expression of stem cell factors was unexpected and unprecedented.

Integration of SRF and Hippo Signaling

Other mediators of cell signaling through SRF are the myocardin related transcription factors MADS boxes, also known as MAL or MKL (Hill and Treisman, 1995; Vartiainen, et al., 2007; Wang, et al., 2002; Lockman, et al., 2004; Miralles, et al., 2003; Yu, et al., 2015). The effect of RhoA on SRF dependent genes is mediated through a TCF independent mechanism (Hill and Treisman, 1995). The myocardin family proteins MRTF-AB provide the link between RhoA-dependent cytoskeletal regulation and SRF-dependent gene expression (Wang, et al., 2002; Lockman, et al., 2004; Miralles, et al., 2003). Mechanistically, MRTF-A associates with G-actin and is thus sequestrated in the cytoplasm under resting conditions. Serum stimulation and signals that activate RhoA to promote actin polymerization lead to MRTF-A dissociation from G-actin, whereupon it translocates into the nucleus and triggers the activation of SRF targets (Yu, et al., 2015).

Dr. Joan Heller Brown and colleagues showed that TEAD also associates with MRTF-A31 (Yu, et al., 2015) overlapping the Myocardin binding site on the SRF's MADS box, to facilitate signaling through actin tread milling leading to rho kinase activation and cell replication (Zaromytidou, et al., 2006). The relationship between YAP, TEAD and the recruitment of other co-factors such as Ncoa3/SRC3 and Esrrb may propel cells further towards cell survival and stem factor activity. For example, SRC3 is an essential coactivator, required to mediate Esrrb function in ES cells. SRC3 interacts with Esrrb via its ligand-binding domain and bridges Esrrb to RNA polymerase II homing complexes (Percharde, et al., 2012). Functionally, SRC3 is critical for both the induction and maintenance of pluripotency and cell replication; thus, their association with SRF, TEAD and YAP may be important in the generation of cardiomyocyte regeneration.

Figure 3:
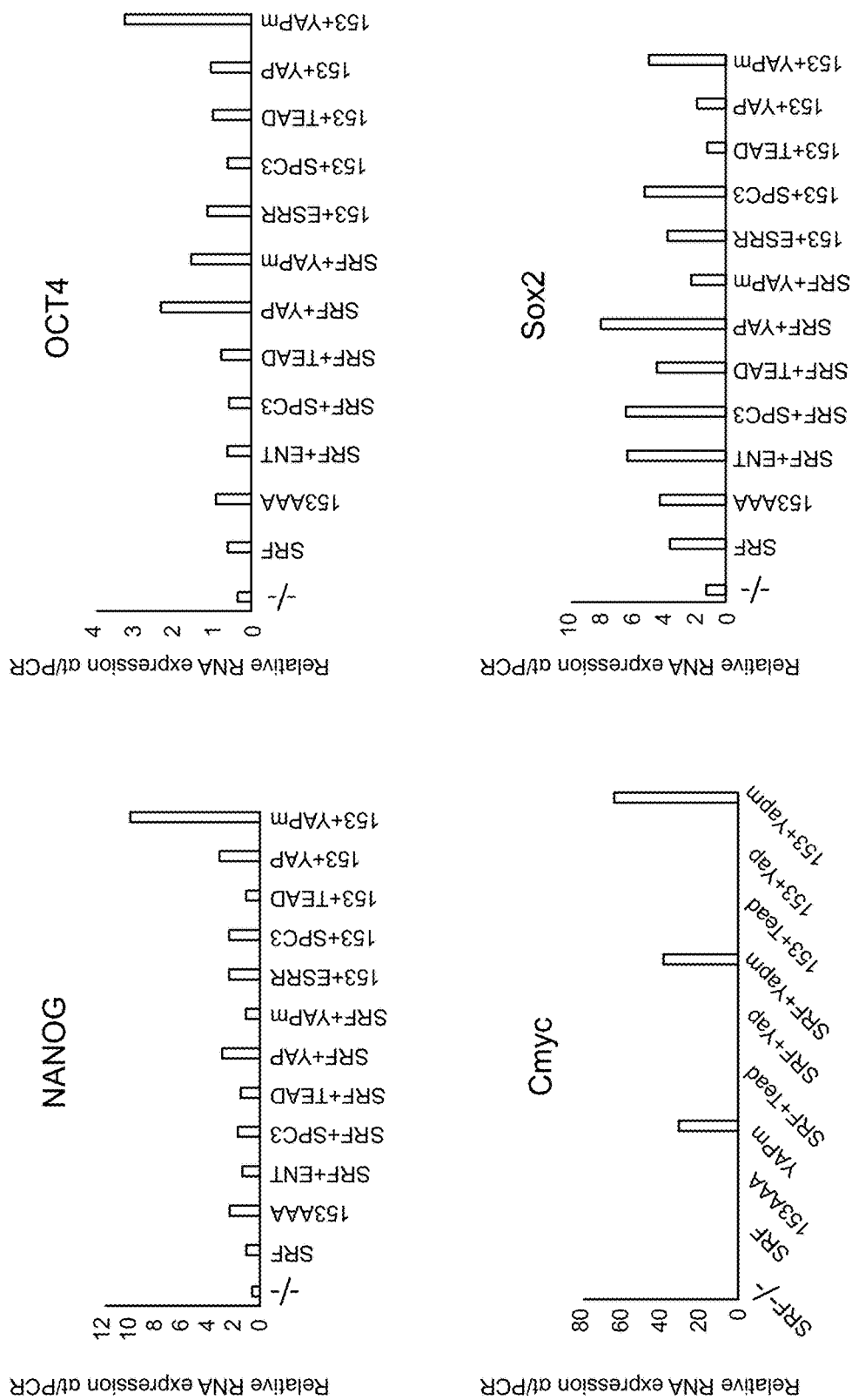
FIG. 3 shows that SRF153 mutant (Stemin) works with YAP1(5SA) mutant to activate Nanog, CMyc, Oct4 and Sox 2.

The schematic model in FIGS. 1A and 1B show a conceptualization of the competition between transcription factors that facilitate proliferation versus cardiomyocyte differentiation through interactomes with the SRF MADS box. Furthermore, it was shown that Stemin worked with the YAP1(5SA) mutant to activate Nanog, CMyc, Oct4 and Sox2 as shown in FIG. 3.

Combination of YAP and SRF Manipulation

YAP/TAZ, as transcription co-activators, do not directly bind to DNA. However, transcriptional enhanced associate domain (TEAD) transcription factors bind to the TEAD binding domain of YAP/TAZ and serve as the main binding platform of YAP/TAZ. The interaction between YAP1 and TEAD1 (TEA domain family member 1), an SRF cofactor that binds directly to SRF's MADS box, is required to stimulate cardiomyocyte proliferation. MRTF-A, another SRF cofactor that binds to the WW domain of YAP/TAZ, potentiates TEAD-YAP transcriptional activity. In activated cancer-associated fibroblasts, YAP-TEAD and SRF-MRTF pathways show mutual dependence. Furthermore, YAP5SA interacts with SRF MADS box through TEADs and MRTF-A, inhibiting interactions between SRF and cardiac specific cofactors to inhibit SRF dependent cardiomyocyte differentiation, to synergistically promote cardiomyocyte proliferation.

Stemin, a triplet alanine mutation at 153 of the N-terminus of the SRF's MADS box (SEQ ID 3), has been shown to inhibit the induction of sarcomere assembly factors involved in cardiomyocyte differentiation. If Stemin could also enhance its binding to cofactors TEAD (TEA domain family member 1) and MRTF-A (Myocardin related transcription factor A), it might promote the interaction between SRF and YAP to manipulate hippo signaling pathways and promote cardiomyocyte proliferation.

Informatics analysis revealed Stemin propelled the induction of stem cell markers, blocked cardiac specified sarcomeric contractile genes, blocked sarcomeric assembly factors, elevated cyclins associated with cell replication and induced mitotic spindle assembly factors. Manipulation of the HIPPO pathway, which regulates organ size, allows cardiac myocytes to divide and regenerate damaged hearts (Heallen, et al. 2013; Leach, et al., 2017). Isolated non-dividing rat myocytes were used to assess whether the SRF mutant, Stemin, requires nuclear YAP1(5SA) to drive cell growth and replication.

Switching off Stemin and YAP1(5SA) mmRNA treatment by the simple replacement of culture media allowed for RNA turnover and enabled us to determine whether replicated stem-like cells revert back to myocyte identity. Proliferating cells are quantitated by flow cytometry. Single cell sequencing of reprogrammed myocytes determine the changes in myocyte specific gene expression. Reversion to adult myocyte gene expression coincides with the reappearance of contractile protein gene signatures and sarcomeres. Therefore, YAP5SA and SRF mutants were investigated for their potential to synergistically reprogram highly differentiated adult cardiomyocyte to cells with a less differentiated, more primitive state and to promote cardiomyocyte proliferation.

Modified Messenger RNA for In Vivo Peptide Expression

Recent progress in modified messenger RNA (mmRNA) synthesis and its utilization in manipulating intracellular protein or peptide synthesis have led to their use for in vivo and in vitro therapeutic applications. Given the post-transcription nature of mRNA, mRNA does not require to be transferred into the nucleus to cause the expression of a target protein. Since the mRNA delivery method will not be affected by the state of the nuclear membrane, transfection efficiency in both dividing and non-dividing cells is guaranteed. Moreover, mRNA-based gene delivery is able to deliver gene combinations with different ratios specifically tailored to patients with a different course of disease.

Unmodified mRNAs are recognizable by the innate immune system of the cells via toll-like receptors, thus promoting the degradation of the unmodified mRNA. Modifying mRNA's secondary structure, by substituting uridine with pseudouridine and replacing cytosine with 5-methylcytidine can produce mRNAs that lead to less recognition by nucleases and toll-like receptors.

Modified mRNAs were synthesized that would provide for the intracellular expression of mutated polypeptide sequences of the SRF core domain or the residues 132-179 of the SRF core domain. Likewise mmRNA that would provide for the intracellular expression of YAP1(5SA) mutants were synthesized as described by Zhao, et al. in 2007).

The utilization of mmRNA for therapeutic applications requires a nontrivial intracellular delivery of the mmRNA. The challenge of efficient intracellular delivery has promoted the development of various delivery systems. Lentiviral vectors have demonstrated inefficient nucleic acid delivery, as well as immunogenicity and safety concerns. In contrast, lipid particles such as liposomes or lipid nanoparticles provide an efficient, non-immunogenic, and safe delivery alternative. For example, Lipofectamine Max™ was shown to have a transfection efficiency approaching about 45% of mmRNA transfection in rat myocytes.

Biosynthesis of mRNA for SRF and YAP1 Mutants

Messenger RNA for SRF (SEQ ID NO: 11) and YAP1 (SEQ ID NO: 13) were modified to provide produce SRF and YAP1 mutants. For example, the mRNA for SRF was modified to produce the mRNA for Stemin (SEQ ID NO: 12).

Synthetic mmRNAs consist of an anti-reverse cap analog (ARCA), 5' and 3' untranslated sequences (UTRs), a polyA tail and the coding DNA of the gene of interest. Antireverse cap analog (ARCA) are modified guanosine nucleotides that are incorporated into the 5' end of the transcript and ensure that synthesis proceeds in only one direction. Capping mRNAs with ARCA simulates the natural capping process and improves transcript stability and enhances translation. mmRNAs are synthesized using modified nucleotides (typically, 5-methycytidine-5'-triphosphate and pseudouridine-5'-triphosphate) (Karikó, et al., 2008; Karikó, et al., 2005).

These modified ribonucleotides increase transcript stability, improve translation efficiency, and decrease the innate immune response. Adding a polyA tail (a long stretch of adenine nucleotides) to the ends of transcripts during synthesis also increases transcript stability and translational efficiency. mmRNAs are typically a fusion between the gene of interest's coding DNA and the 5' and 3'UTRS from a different gene such as beta-globin; the 5' and 3'UTR sequences that are typically selected are chosen because their sequences are known to increase transcript stability when they are used in place of the native UTRs of otherwise unstable transcripts. Stemin and YAP1(5SA) mRNA were synthesized. To provide these mRNAs additional selectivity, the substitution of 5'UTR and 3'UTR of the cardiac alpha actin gene onto the Stemin and YAP1(5SA) mmRNA to enhance the selective translatability and stability in cardiac myocytes.

Transcriptome Analysis

Gene profiling experiments of FACS sorted myocytes are used to compare gene expression patterns among the synthetic mmRNA treated cardiomyocytes. Myocytes from controls versus synthetic Stemin and YAP1(5SA) induced myocytes were FACS isolated following washing and refeeding of the cells to remove synthetic RNA in the switched off myocytes.

Stemin in synergy with YAP1(5SA) induces many stem cell marker genes, such as, Nanog, Oct4, Sox2 and C-Myc as shown in FIG. 3; inhibits cardiac myocyte specified genes such as sarcomeric contractile proteins; and represses sarcomeric assembly factors, such as Actinin2, Nebulin, Titin, Myomesin, Obscurin Filamin, Smyd1 and SNF1-K2. In addition, evidence is provided that Stemin and YAP mutant fostered cell replication and the up regulation of cyclins B1, Cdk1 and the other spindle assembly factors such Bub 1 and Aurora Kinase A/B.

Switching off synthetic RNA activity will require simple replacement of culture media. Replicated myocytes are allowed to re-differentiate over time in myocyte differentiation media that does not contain fetal bovine serum (FBS) to allow investigators to determine if myocytes revert to their myocyte identity or differentiated state after synthetic RNA induction.

Transduction of Cardiomyocytes with Synthetic mmRNAs

Rat cardiomyocytes were transduced with synthetic mRNA of Stemin alone (SEQ ID NO: 12), YAP1(5SA) alone, and a combination of the two to determine if Stemin and YAP interacted in their cellular response.

Figure 5:
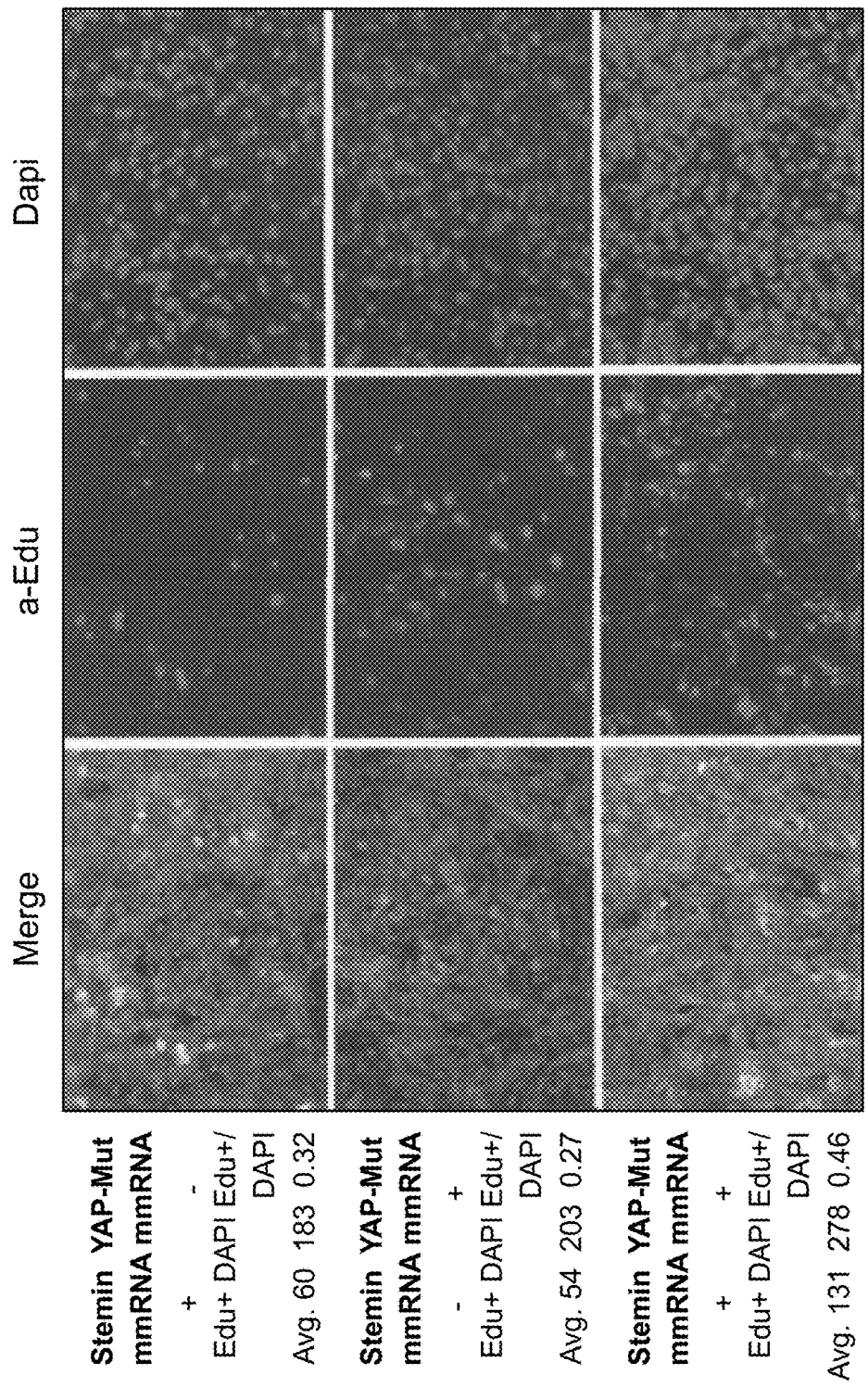
FIG. 5 illustrates DNA replication in rat cardiomyocytes after transfection with Stemin mmRNA or YAP-mutant mmRNA alone or both together.

Myocytes were assessed for expression of Troponin T (TnnT) and aEdu staining by immunofluorescence assays. Nuclei were stained with DAPI. Quantification of immunofluorescence microscopic images was done with imageJ™ software. An equal number of myocytes were plated in triplicate for each transfection condition. At the end of day three after a 6 hour pulse of aEdu, the cells were fixed and the fluorescently labeled cells counted. The number of troponinT marked myocytes stained with anti TnnT that were also labeled for DNA synthesis with a-Edu (RED) and coincided with nuclear Dapi stain were quantitated (see FIG. 5).

Virtually all of the aEdu/Dapi stained nuclei lay within TnnT stained cells (green). Stemin induced DNA replication, in 32% of the myocytes. Next the response to YAP1 (5SA) synthetic mRNA was evaluated, following an identical protocol in which 27% of the myocytes stained with aEdu/Dapi. However, the combination of Stemin and the YAP1(5SA) transfection of the cardiac myocytes increased the co-staining of the aEdu+/Dapi marked myocytes by 46% of the total number of cells. This is a likely underestimate since replicated cells may have synthesized DNA before the pulse of aEdu. Nuclei, co-stained with aEdu (Red) and Dapi (Blue) were observed, as pink in the merged images. Also, disorganized TnnT2 stained myofilaments (green) were observed with labeled aEdu/Dapi nuclei. Therefore, a short pulse of Stemin and or Yap1(5SA) induced myocyte division, in at least 27% to 46% of rat cardiomyocytes.

To assess a genetic gain-of-function, investigators transfected SRFwt, or SRF153(A3)(Stemin), with constitutively active mutant YAP1(5SA), TEAD, SRC3 into murine SRF null ES cells that had been reprogrammed to cardiomyocytes. FIG. 3 shows the induction of Nanog, Oct4, CMyc and Sox2 by SRF153(A3) and YAP1(5SA) mutants. These factors were detected on protein blots with specific antibodies. The co-infection of YAP1(5SA) and SRF153(A3) in SRF null ES cells showed a synergistic co-induction of Nanog, Oct4, C-Myc and Sox2. The addition of TEAD, ESRR and/or SRC3, and with SRFwt or SRF mutants were not as effective as the addition of the YAP mutant. Thus, the SRF mutants had a synergistic effect with the YAP mutant to drive stem cell factors.

Bioinformatic analysis revealed the upregulation of multiple cell cycle gene clusters with the co-expression of SRF mutants and YAP5SA; while gene clusters associated with cardiomyocyte differentiation, sarcomeric assembly and cardiac muscle contraction were profoundly down regulated. To identify the underlying mechanism of how works as a different transcription factor compared with SRF, the ATAC-seq of the cells under SRF mutant and YAP5SA treatment was performed to create a bioinformatics landscape of interactomes of SRF mutants. ATAC seq (Assay for Transposase-Accessible Chromatin using sequencing) is a technique used in molecular biology to assess genome-wide chromatin accessibility, i.e. which genes are being actively transcribed.

Rat neonatal cardiomyocytes were harvested 32 hours, 40 hours, and 48 hours after treatment with SRF mutant mRNA, YAP5SA mRNA, and a combination of SRF mutant and YAP5SA mRNA delivered by Lipofectamine MessengerMAX™ (ThermoFisher). RNA was extracted and underwent quality control assessment using the RNA tape on Tapestation4200™ (Agilent) and were quantified with Qubit Fluorometer™ (ThermoFisher). Kallisto™ was used for pseudo alignment and transcript quantification.

Differential gene expression quantification was performed and the differentially expressed genes (DEG) was determined with fold change >1.5 and P-FDR-adjusted <0.1 genes (FDR: False Discovery Rate) with more than 1 Reads Per Kilobase of transcript, per Million mapped reads (RPKM), under the test conditions as compared to the controls. Gene set enrichment analysis (GSEA) was conducted using javaGSEA2-3.0™. Gene ontology analysis was performed using Bioconductor-cluster Profiler™ packages. All the tables and figures in RNA-seq analysis were plotted by R-studio (3.6.0). Heat maps were plotted using R "pheat map" package.

Based on the GO-term analysis, several heat maps were generated to identify specific genes in the unregulated and down regulated terms. All gene lists, which were used for plotting heat map for representing expression alteration of specific Gene Ontology (GO) terms, were extracted from MGI (http://www.informatics.jax.org/) or RGD (https://rgd.mcw.edu/rgdweb/homepage/) database.

Mitotic spindle forms during cell division and separate sister chromatids between daughter cells. RNA-seq data showed that several spindle assembly factors such as Bub 1 (mitotic checkpoint serine/threonine-protein kinase BUB1) were upregulated after the synthetic RNA induction, suggesting the neonatal cardiomyocytes were pushed into cell division by the synthetic mRNA induction.

Genes involved in cytokinesis were highly unregulated. One of the unregulated genes, PLK1 (Polo-like kinase 1), has been reported to promote contractile ring formation, cleavage furrow ingression, and foster RhoA accumulation at the equator. ANLN (Anillin) was also highly upregulated in the combination treatment group. The presence of ANLN is required in multiple stages of cytokinesis, and ANLN acts as a key mediator of cytokinesis. Upregulation of crucial cell cycle genes such as Plk1 and ANLN suggested that SRF mutants and YAP5SA fostered cell replication by promoting several steps of the cell-division cycle of the cardiomyocyte.

Genes in the GO term of Nuclear division were also profoundly unregulated. When CCNB1 (Cyclin B1) gene product complexes with CDC2 (Cell Division Cycle 2) to form the maturation-promoting factor (MPF) the necessary proper control of the G2/M transition phase of the cell cycle is initiated. CDC20 (Cell Division Cycle 20) acts as a regulatory factor interacting with several other factors at multiple points in the cell cycle. Upregulation of crucial genes such as CCNB1 and CDC20 suggested that SRF mutants and YAP5SA also promote nuclear division to foster cardiomyocyte division.

Notably, although genes involved in spindle assembly, cytokinesis, and nuclear division were only slightly unregulated in the SRF mutant treatment group compared to the YAP5SA mRNA treatment group, synergy was clearly observed between the SRF mutants and YAP5SA mRNA treatment groups. Cell cycle factors were robustly unregulated in the groups with the combination treatment at all three different time points, with a much higher fold change than SRF mutant and YAP5SA single treatment groups.

Cardiac specific factors were identified to be down regulated after mRNA treatment. SRF mutants alone could decrease the expression level of specific cardiac specific genes, but the groups with the SRF mutant and YAP5SA combination treatment at all three time points presented lower expression of the cardiac differentiation factors than both single mRNA treatment groups, which may result from the synergistic effect of SRF mutants and YAP5SA.

Genes involved in cardiac muscle cell differentiation were down regulated in the combination treatment group. ACTN2 (Actinin Alpha 2) encodes a muscle-specific alpha actinin isoform that is expressed in cardiac muscles and skeletal muscles. MYH6 (Myosin Heavy Chain 6) is one of the two alpha heavy chain subunits of cardiac myosin. Down regulation of crucial genes contributing to cardiac muscle cell differentiation such as Actn2 and Myh6 suggested that SRF mutants and YAP5SA pushed cardiomyocytes into a less differentiated, more primitive stage.

Heat maps of heart contraction genes were also generated based on RNA-Seq data. TNNT2 (Cardiac muscle Troponin T) which is a part of the Troponin complex is responsible for binding tropomyosin to regulate calcium binding and contractility of cardiomyocytes. TNNI3 (Troponin 13, Cardiac Type) is another one of the three subunits that form the Troponin complex of the thin filaments of striated muscle in cardiomyocytes. The Troponin complex regulates muscle contraction. Both Troponin T and Troponin I are crucial cardiac specific markers. Down regulation of these genes suggested that cardiomyocytes were brought back to a less differentiated state in order to promote cardiomyocyte proliferation.

Thus the interactome signatures that were associated with Stemin and YAP5SA were both over expressed in the rodent cardiomyocytes. Bioinformatic analysis revealed the upregulation of multiple cell cycle gene clusters with the co-expression of SRF mutants and YAP5SA, while gene clusters associated with cardiomyocyte differentiation, sarcomeric assembly, and cardiac muscle contraction were profoundly down regulated.

Treatment for Heart Disease

Some embodiment of the invention will use mutant SRF or a mutated SRF polypeptide in conjunction with a mutant YAP1 or a mutated YAP1 polypeptide to treat heart disease. However, preferred embodiments of the invention described herein combine the use of mmRNAs designed to produce intracellular YAP1 and SRF mutants in the treatment of heart disease. Therapeutic agents or compositions envisioned herein include a modified messenger RNA for expressing Stemin or a modified SRF polypeptide, as well as a modified messenger RNA for expressing a modified YAP polypeptide, and a liposomal delivery agent.

SRF Mutant and YAP5SA Repair of Infarcted Adult Mouse Hearts

C57BL/6J mice of both genders were housed and studied in strict accordance with national standards.

Myocardial Infarction Model. Myocardial infarction (MI) was induced by left anterior descending (LAD) ligation on the starting day or day (+0) of the experiments (i.e., −0.5 hours). Mice were put under 1.5% isoflurane inhalation anesthesia and body temperature kept at 36° C. while the surgeries were conducted. A 3% isoflurane was initially used to anesthetize the animal for intubation. A 20 G intravenous catheter connected to a ventilator was inserted into the mouse trachea through the oral cavity, conducting artificial ventilation at 120 strokes/min, 20 mL/kg/stroke using room air.

The mouse heart was exposed through the thoracic cavity opened through the left fourth intercostal space. An 8-0 polypropylene ligature was used to tie the LAD by fine, smooth tipped forceps. Alteration of heart color was observed after the ligation of the LAD. A 6-0 polypropylene ligature was used to suture the animal thoracic cavity by layered stitches. The lungs were inflated to displace air. Animals were removed from artificial ventilation and remained in a supervised setting until fully conscious. Animals in both experimental groups and control groups were housed in separate warm cages until recovery.

In Vivo mRNA Delivery. Synthetic mRNAs were injected into the left ventricular (LV) myocardium 5 minutes after the LAD ligation of mouse heart in an open-chest surgery on the starting day of the experiments. One hundred (100) µg mRNA together with Lipofectamine MessengerMAX™ of a total volume of 60 µL was injected into the left ventricle myocardium of the mouse heart.

Myocardial Echocardiography. Myocardial echocardiographs (echos) were conducted under anesthesia with 1% isoflurane. Each mouse was placed on a warm pad to keep the body temperature around 36° C. Warmed echo gel was placed on the chest of the mouse and the heart was imaged with a linear transducer. The heart rate was controlled at a similar level within each strain of measurement. LV ejection fraction (EF), LV fractional shortening (FS), stroke volume, LV septal thicknesses, heart rate, left ventricular posterior wall, and left ventricle internal dimension were measured.

Figure 6:
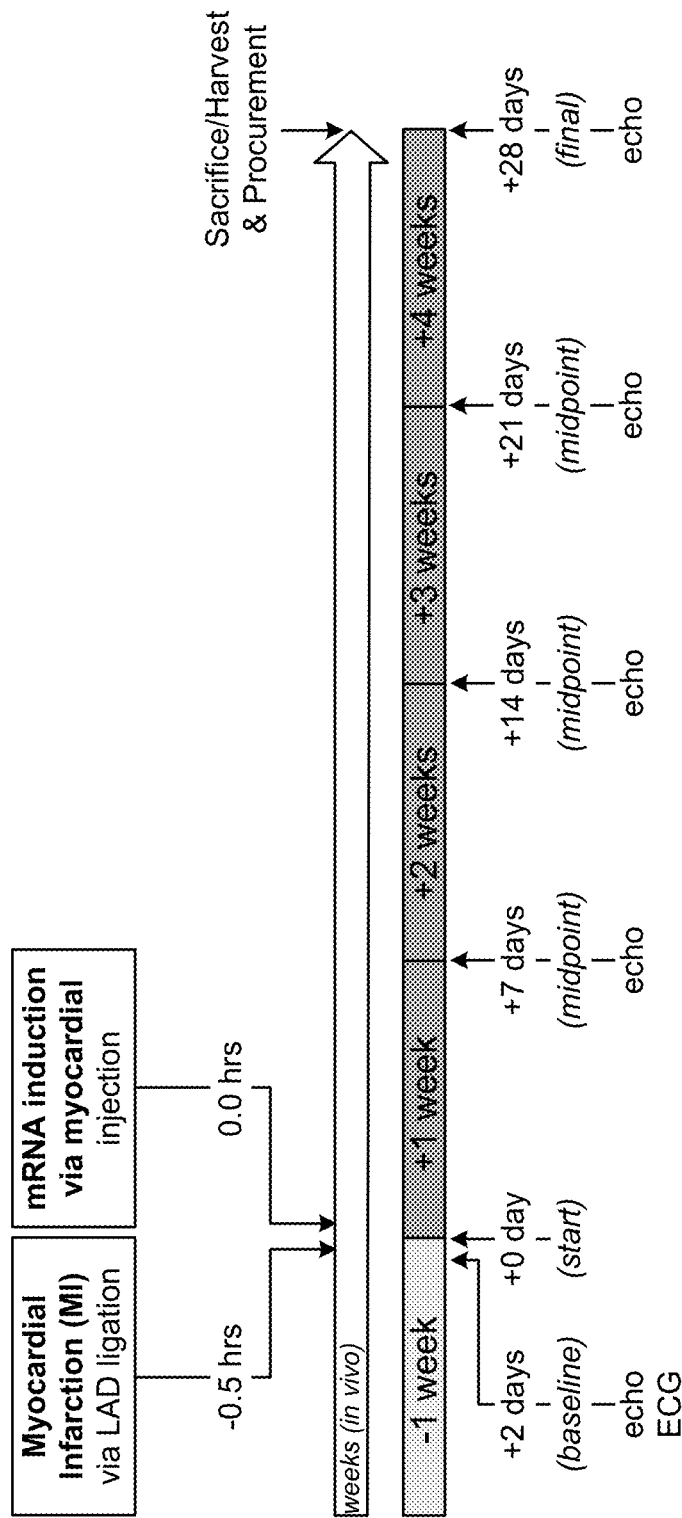
FIG. 6 shows the experimental timeline for the in vivo treatment of infarcted adult mouse hearts with Stemin mmRNA and YAP-mutant mmRNA.

Myocardial echocardiography was measured on day (−2) (i.e., −48 hours; baseline), first week (+1) (i.e., +7 days; midpoint), second week (+2) (i.e., +14 days; midpoint), third week (+3) (i.e., +21 days; midpoint), and fourth week (+4) (i.e., +28 days; final) time-point intervals relative to the injection of the mRNA as shown in FIG. 6.

Tissue Harvesting and Sectioning. At the conclusion of the in vivo assessments, animals were sacrificed, and their heart tissue harvested. After each mouse was euthanized with $CO_2$, the intact heart was immediately removed, soaked in phosphate buffered saline (PBS), and perfused with PBS through the aorta to remove the blood in the heart. The heart was fixed in 4% paraformaldehyde overnight and transferred to 70% ethanol before embedment. Histo-Clear™ was used to wash the tissue before embedded in liquid Paraplast™ (Sigma-Aldrich). The heart was embedded in a sagittal direction and frozen at −20° C. before being sectioned. The microtome was set to section the tissue at 10 µm sections.

Tissue Staining. The slides were washed with ethanol, Histo-Clear™, and water before antigen retrieval. Slides were then soaked and boiled in 10 mM sodium citrate (pH 6.0) at 95° C. in a water bath. A 5% goat serum was used to block the slides. The heart sections were then stained with hematoxylin and eosin.

In Vivo EdU Assay [DNA synthesis]. EdU (10 µg/g of mouse body weight) was injected via subcutaneous injection at 8 hours prior to sacrifice. The intact heart was fixed in 4% paraformaldehyde, stored in 70% ethanol and then embedment into paraffin for histological assessment. The heart was cross-sectioned and EdU was detected by Click-iT EdU Cell Proliferation Kit™ (ThermoFisher). Slides were visualized by a Leica™ SP8 confocal microscope.

DAPI and EdU Quantification. DAPI staining and EdU incorporation was detected by a Leica™ SP8 confocal microscope. Confocal microscopy pictures were analyzed by Image J™ to get the quantification analysis on DAPI staining and EdU incorporation. Pictures were divided into 90 equal divisions and the integrated density was measured for each division. The same threshold was used for all the divisions in different treatment groups.

Figure 7:
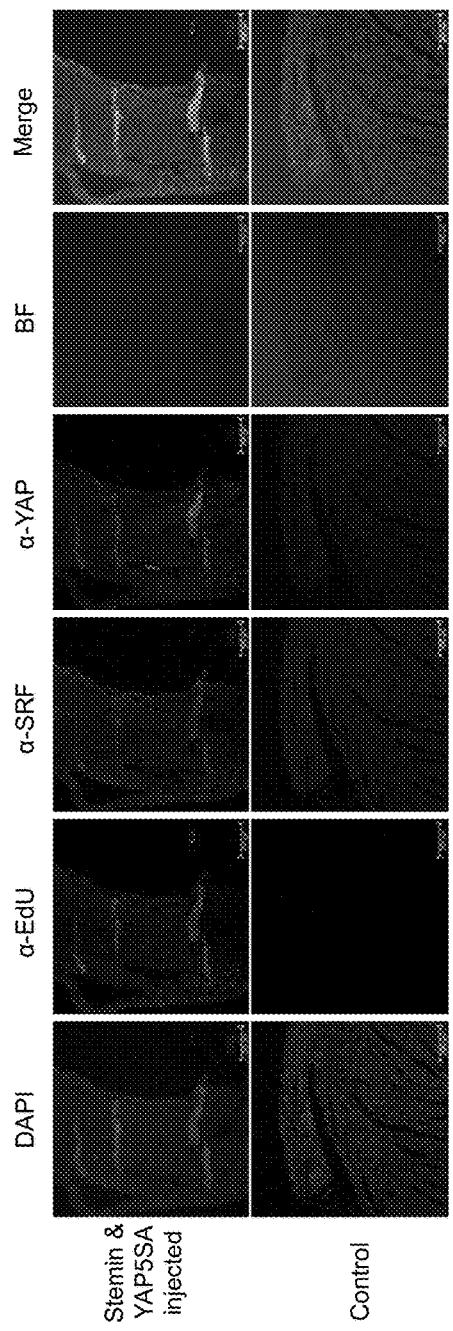
FIG. 7 shows the results of DAPI staining and EdU incorporation into adult mouse hearts injected with Stemin mmRNA and YAP-mutant mmRNA.
Figure 7:
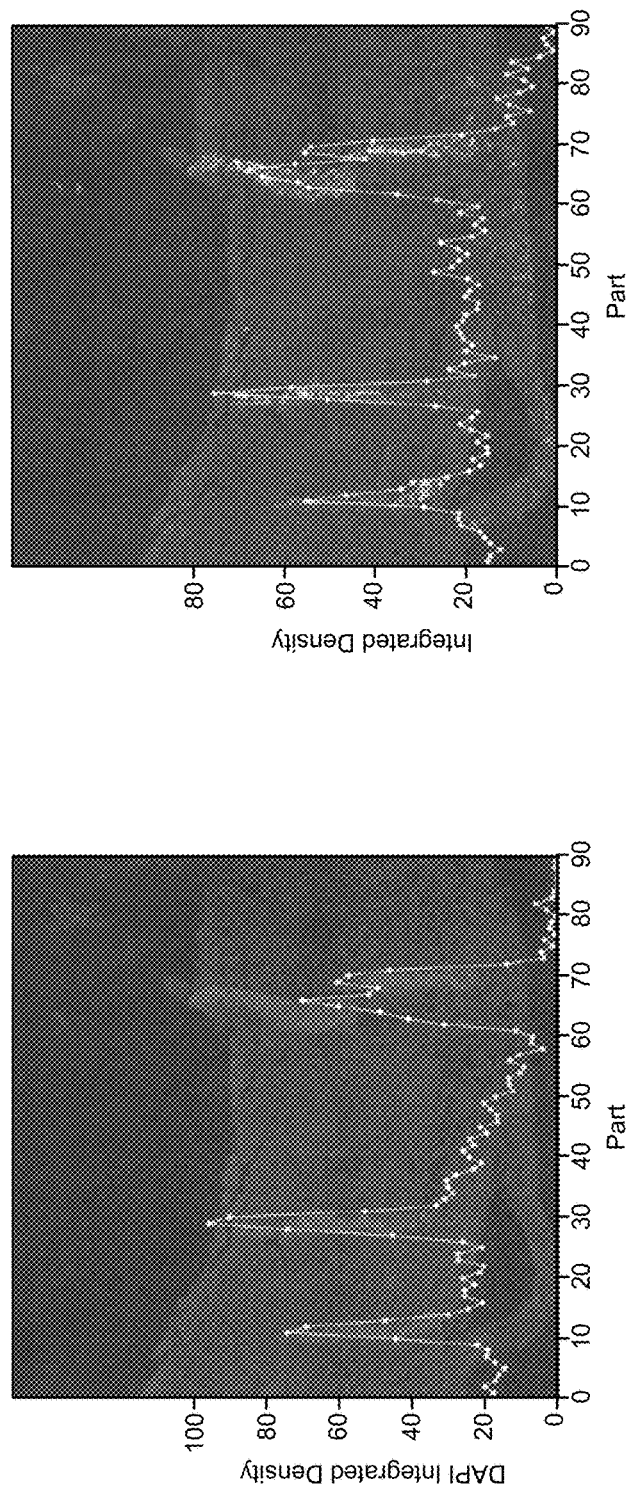

Results. A short-term 24 hour assay was initially done to test if the injection of Stemin mRNA and YAP5SA mRNA could promote cell proliferation and EdU incorporation in adult mouse heart in vivo. EdU was injected into the test animals 8 hours before sacrifice to give the animals an eight-hour EdU pulse. EdU incorporation was detected on the slides with heart cross-sections (illustrated at the top of FIG. 7). An increment of DAPI signal around the needle tracts in the Stemin and YAP5SA mRNA treatment group was detected, which indicated an increase in cell number around the needle tracts. EdU-labeled nuclei gathered mostly along the needle tract in the combination treatment group, suggesting that the mRNA injection promoted EdU incorporation in the adult mouse heart in vivo. EdU incorporation was undetectable in the control group.

The alteration of DAPI and EdU incorporation were then quantified using the Image J™ software. Confocal microscopy pictures were divided into 90 equal divisions and integrated density was measured and plotted. Four peaks of integrated density were detected and plotted for both DAPI and EdU (see FIG. 7) staining in the combination mRNA treatment groups right at the three needle tracts, with the last two peaks forming a wide peak. The peaks of DAPI and EdU incorporation indicated that the Stemin and YAP5SA mRNA injection could increase cell number and promote EdU incorporation in the left ventricle of adult mouse heart in vivo.

After confirming the short-term effect of Stemin and YAP5SA mRNA in promoting cell proliferation and EdU incorporation in adult mouse heart in vivo, a long-term experiment was performed to detect if the injection of Stemin and YAP5SA mRNA would improve the mouse heart function after myocardial infarction and repair of the damaged heart.

Echocardiography was done two days before surgery to create a base line of the heart function in both experimental and control groups. Myocardial infarction was induced by LAD ligation before mRNA injection through an open-chest surgery on the starting day of the experiment (FIG. 6). LV ejection fraction (EF), LV fractional shortening (FS), stroke volume, LV septal thicknesses, heart rate, left ventricular posterior wall, and left ventricle internal dimension were measured every seven days after injection. The mice were sacrificed on the 28th day post injection to harvest the heart for imaging.

Figure 8A:
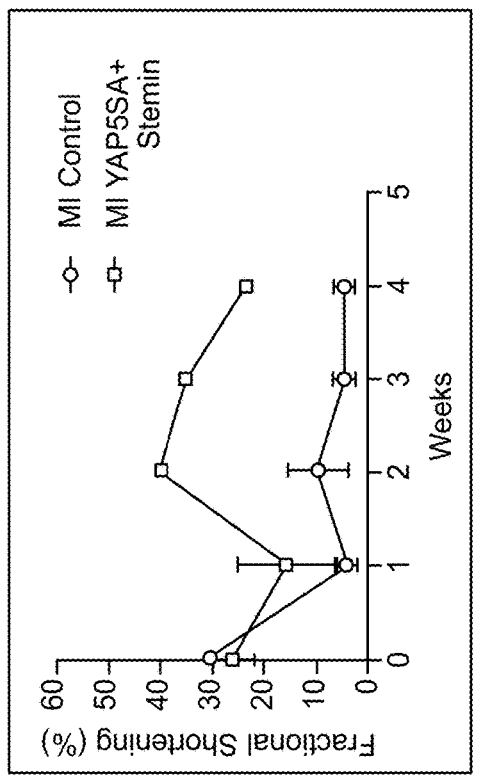
FIG. 8A-8L illustrate the cardiac function in infarcted adult mouse hearts injected with Stemin mmRNA and YAP-mutant mmRNA and in control infarcted adult mouse hearts that were not injected with Stemin mmRNA and YAP-mutant mmRNA.
Figure 8B:
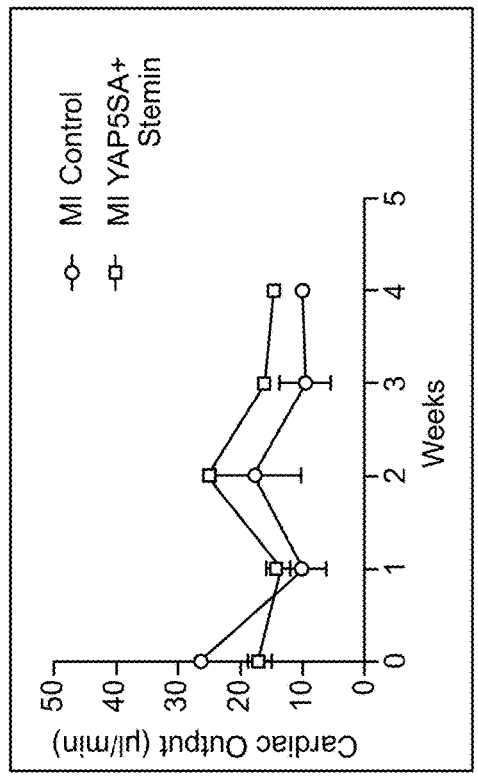
Figure 8C:
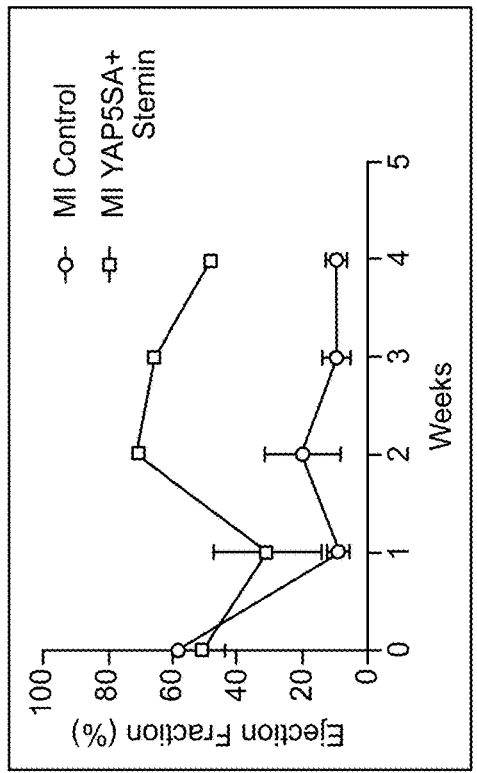
Figure 8D:
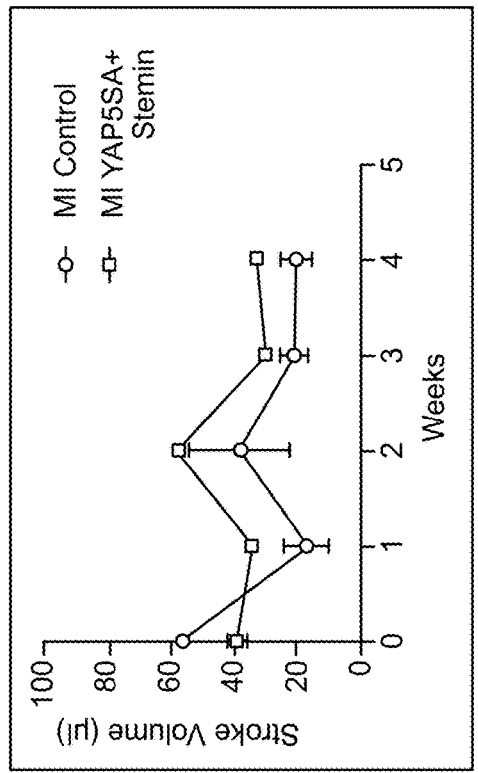

Ejection fraction and fractional shortening dropped in both control and Stemin and YAP5SA mRNA injection groups due to the myocardial infarction induction in the first week (FIGS. 8A and 8B). The ejection fraction and fractional shortening at week 2 were increased more than 60% and 40% respectively in the combination mRNA injection group, and were kept at a higher level compared to the control, which indicated a significantly improved heart function promoted by Stemin and YAP5SA mRNA injection. Stroke volume and cardiac output in the combination treatment group, reflecting the column of blood which moves through the LV outflow tract during each systole, was higher than control group from the first week post-surgery, and an increase can be observed in the second week post-surgery in both groups (FIGS. 8C and 8D). Cardiac output was calculated by stroke volume times heart rate.

Figure 8E:
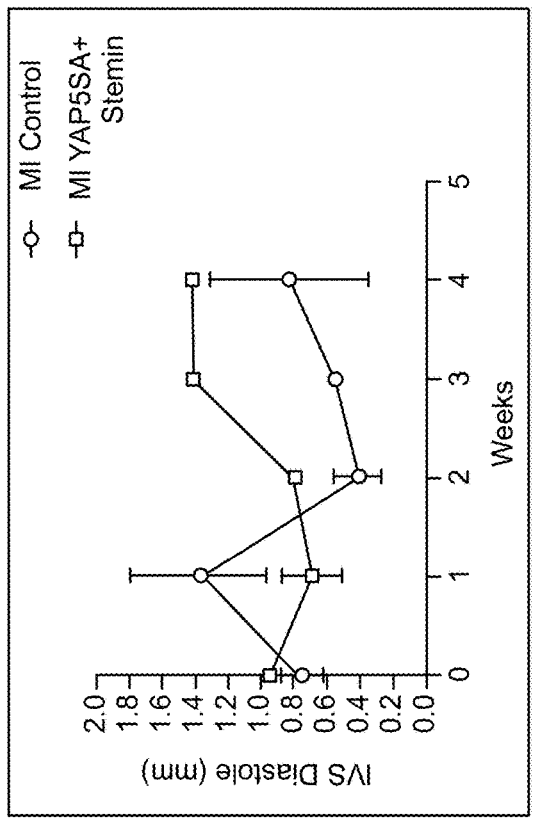
Figure 8F:
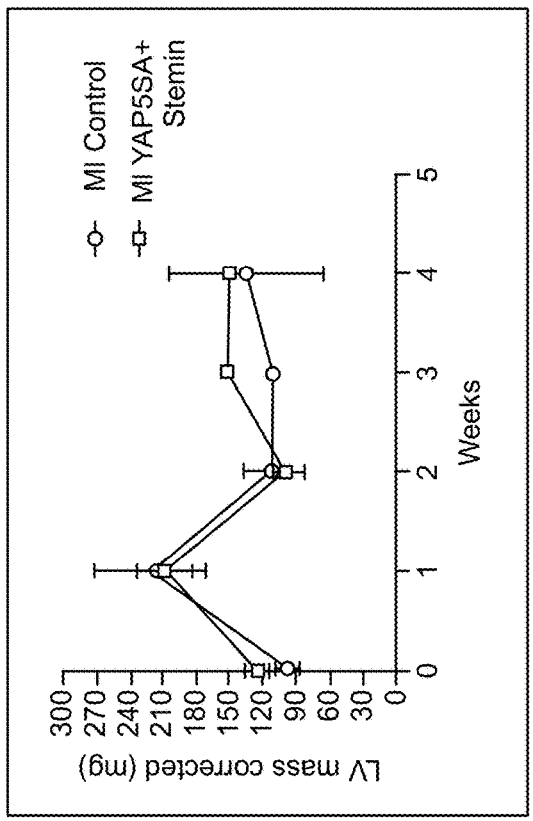
Figure 8G:
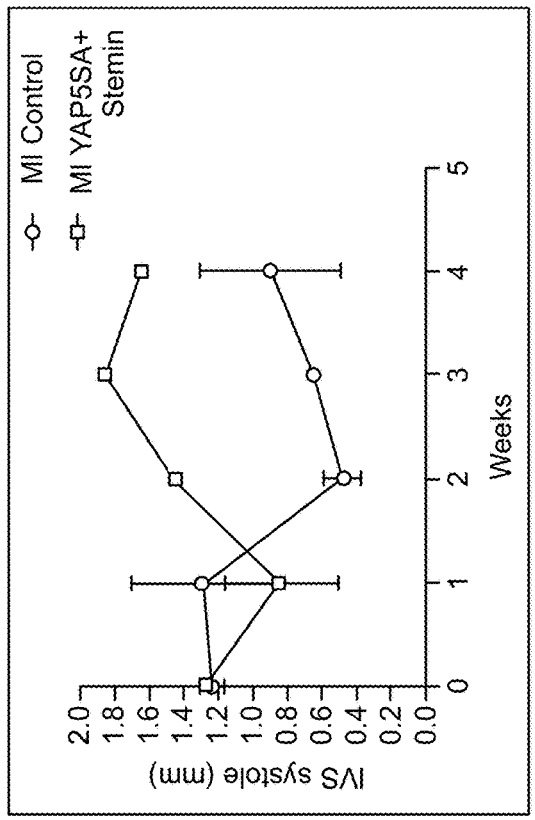
Figure 8H:
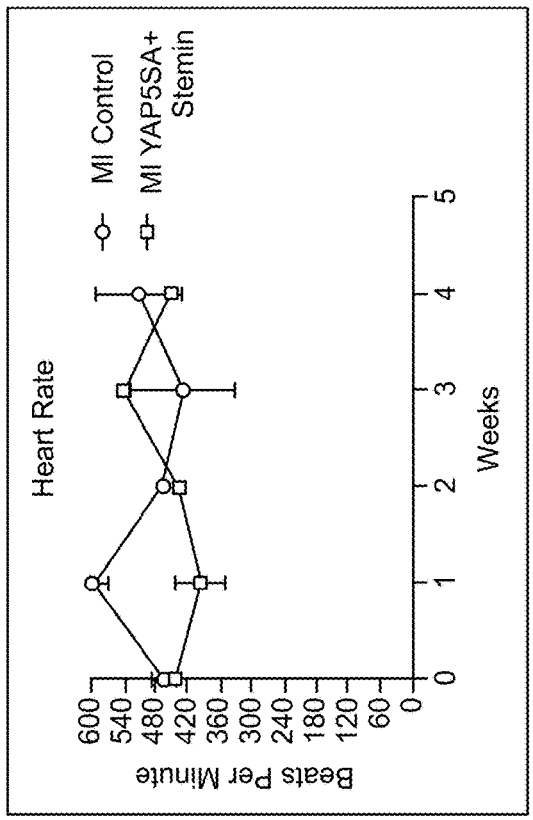
Figure 8J:
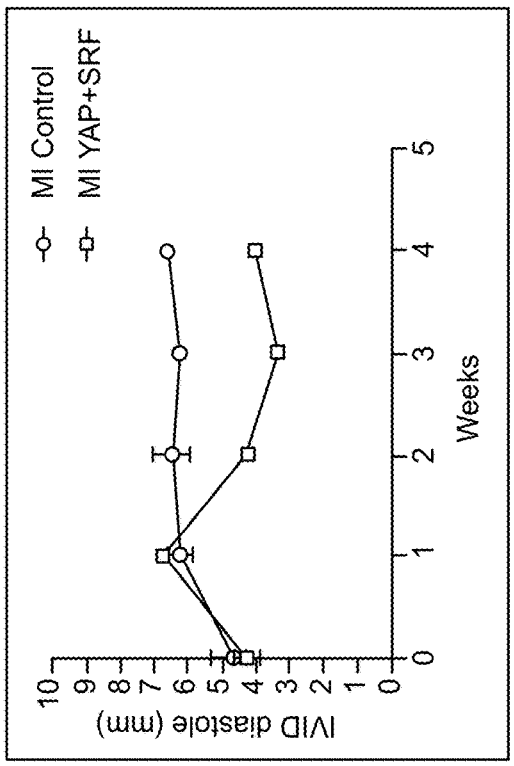
Figure 8L:
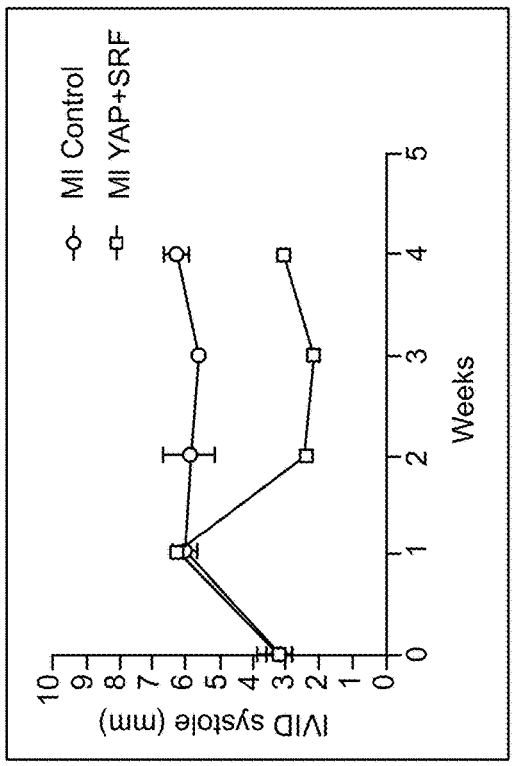
Figure 8I:
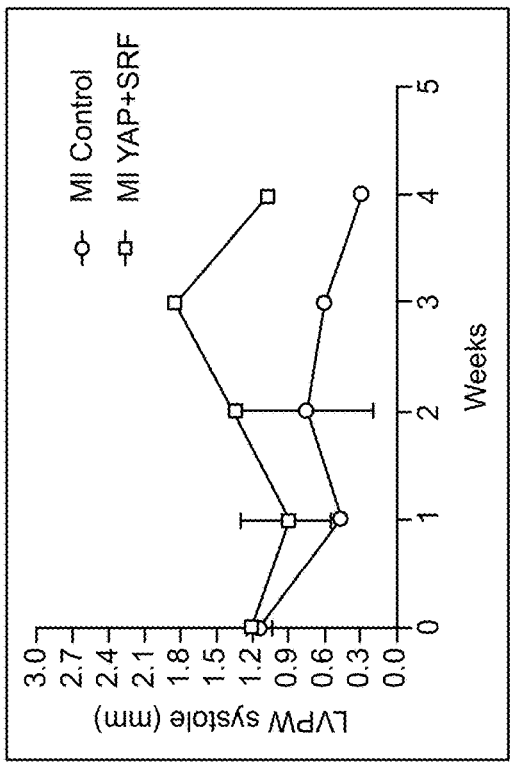
Figure 8K:
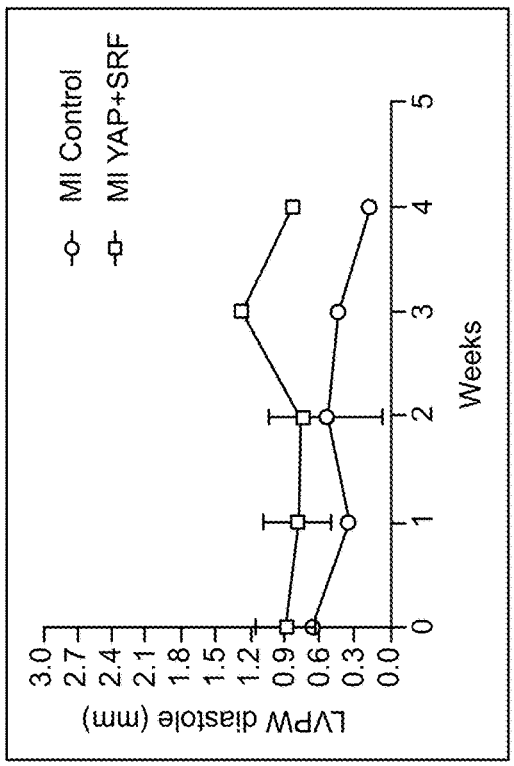

LV interventricular septal thicknesses (IVS) of the combination mRNA treatment group was narrower than the control group at the first week post-surgery, but an increase in IVS at both systole and diastole was observed at the second week after injection in the combination group, while the IVS of control group dropped to a relatively low level (FIGS. 8E and 8F). The heart rate of both groups was within an acceptable range, and the LV mass correction in the combination injection group was close to the control group, which indicated that there was no abnormal LV mass change (FIGS. 8G and 8H).

Left ventricular posterior wall (LVPW) of the combination treatment group was observed to be higher than that of the control group at systole and diastole (8I and 8K). There displayed an increase in LVPW at the fourth week in the combination treatment group compared to the second week, and accordingly, left ventricle internal dimensions (LVID) were decreased in the combination injection group (8L and 8J). This indicated a recovery in wall thickness was promoted by Stemin and YAP5SA mRNA injection.

Figure 9:
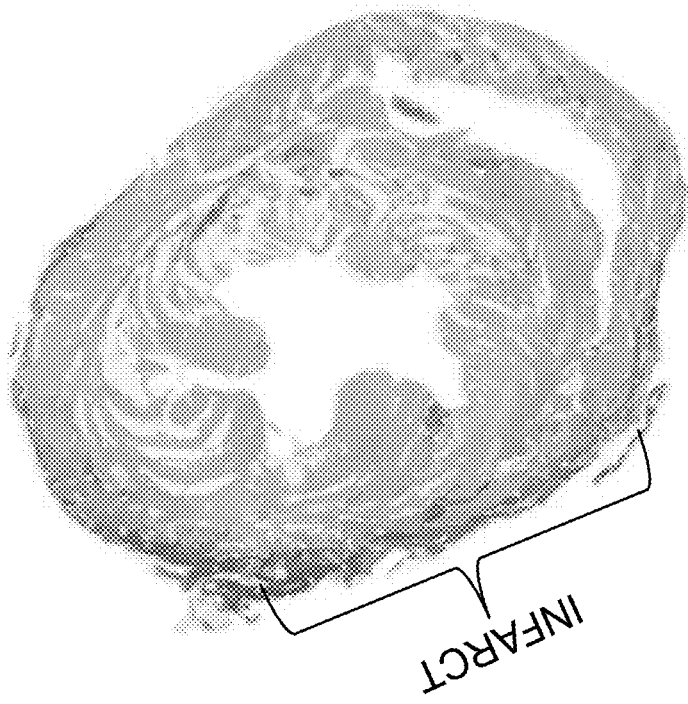
FIG. 9 illustrates the infarct zone in infarcted adult mouse hearts injected with Stemin mmRNA and YAP-mutant mmRNA and in control infarcted adult mouse hearts that were not injected with Stemin mmRNA and YAP-mutant mmRNA.
Figure 9:
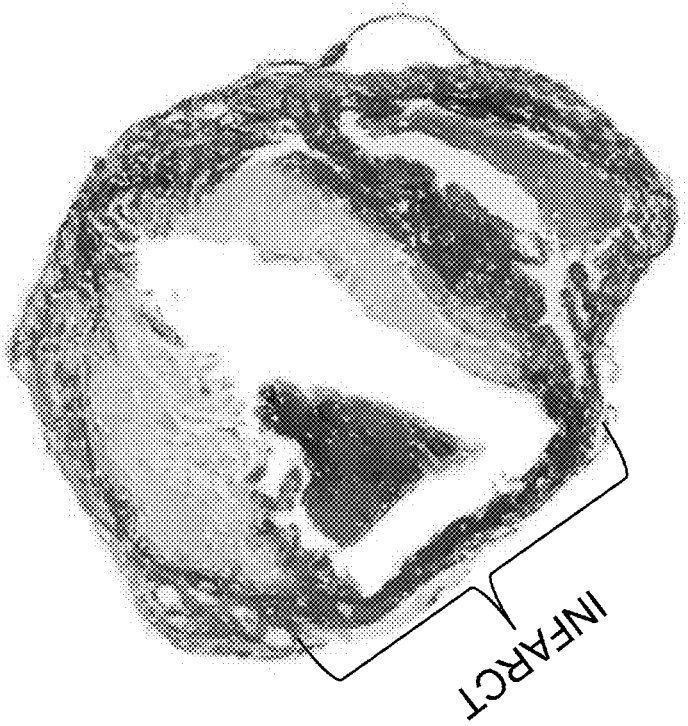

The mouse hearts were harvested at the end of the four weeks of the long-term experiment. Tissues were sectioned and stained with hematoxylin and eosin to observe morphological change in the heart after surgery and injection. The infarct zone can be seen and marked in the control group heart, while the infarct zone in the Stemin and YAP5SA was undetectable in all the sections of the combination treatment group (FIG. 9). This indicated that the injection of Stemin and YAP5SA after mouse myocardial infarction induction could repair the infarcted adult mouse heart in vivo.

Thus, injections of Stemin/YAP1 mmRNA repaired mouse infarcted hearts by increasing myocyte replication and reducing wall thinning. As the myocytes gained maturity after treatment, the heart gained in its pumping function.

Exemplary Embodiments of the Therapeutic Agent for Heart Disease

Embodiments of the composition of the therapeutic agent to be used in treating heart disease include a modified messenger RNA for expressing a SRF mutated polypeptide, a modified messenger RNA for expressing a modified YAP polypeptide, and a liposomal delivery agent.

Preferred embodiments of a mmRNA designed to produce an intracellular mutant of the amino acid residues 147-153 of the core domain of SRF (SEQ ID 5) include the mutants 141A3 (SQ ID 5), 144A3 (SQ ID 6), 147A3 (SQ ID 4), 150A3 (SQ ID 7), and 153A3 (SQ ID 3). A preferred embodiment of the mmRNA for expressing a modified YAP polypeptide is the YAP5SA mRNA reported by Zhao, et al. in 2007.

A number of methods can be used to deliver the mmRNAs to the cells, such methods include liposomes, polymers, microspheres, gene therapy vectors, and naked DNA vectors. For example, transducing viral (e.g., retroviral, adeno-viral, lentiviral, and adeno-associated viral) vectors have often been used been used because of their high efficiency of infection and stable integration and expression.

Lipofection, also known as "lipid transfection" or "liposome-based transfection," uses a lipid complex to deliver DNA to cells and is the preferred embodiment of the mmRNA delivery system. Lipids are a broad class of fat-soluble biomolecules. The cell membranes of animal cells are composed of a bilayer of phospholipids with hydrophilic surfaces facing the cytoplasm and extracellular environment. Lipofection technology uses tiny vesicular structures called liposomes that have the same composition as the cell membrane. The mRNA to be introduced into the heart is encapsulated into a liposome. Depending on the liposome and cell type, the liposome can be endocytosed or directly fuse with the cell membrane to release the mRNA into the target cell. There is a number of liposomal based transfection agents, but Lipofectamine™ or Lipofectamine Messenger MAX™ are common transfection reagents, produced and sold by Invitrogen. Lipid nanoparticles (LPNs) have also been designed to provide a safe, safe alternative for protecting mRNAs from degradation and immune activation and to facilitate their release from endosomal compartments to the cytosol. Recently, LPNs have been specifically targeted for cell specific expression by coating the LNPs entrapping the mmRNAs with monoclonal antibodies.

One preferred embodiment of the therapeutic agent includes a Stemin mRNA, a YAP5SA mRNA, and a Lipofectamine transfection agent.

Exemplary Embodiments for Treating for Heart Disease with the Therapeutic Agent

The loss of cardiomyocytes underlies most causes of heart failure. Normal repair processes are inadequate to deal with extensive myocardial damage. The ability to regenerate myocytes in a patient by enhancing the replication of cardiomyocytes with the therapeutic agents described above will be a new standard of care for damaged heart muscle in the future. The therapy described herein will increase the number of myocytes derived from the patient's own heart to increase heart wall thickness following an infarct or increase function in the setting of heart failure. Although this treatment is designed to treat patients having suffered from a myocardial infarction or other type of heart disease, it may also be used to treat pediatric cardiac diseases, to repair congenital cardiac birth defects, and to expand the heart wall in hypoplastic hearts.

The heart tissue of a patient with heart disease will be visualized using echocardiography and/or ultrasound to identify areas of infarct or tissue damage. The mRNAs of the therapeutic agents are introduced into the border of the damaged cardiac tissue by a cardiac catheter. Typically, the therapeutic agent is injected at multiple sites in the border area between visualized healthy and damaged tissue. A typical treatment will include 1-10 injection sites as the catheter is moved to different areas of cardiac muscle damage. Echocardiograms will be performed to assess the success of the treatment.

In treating myocardial infarction patients, the treatment regimen will typically begin when the myocardial infarction has been diagnosed or within two weeks of the diagnosis. However, the use of the therapeutic agent to treat infracted heart tissue may be useful over a much longer extension of time. Similarly, the described treatment regimen may be helpful in the treatment of a number of types of heart disease.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

1. Ahuja P, Perriard E, Perriard J-C, Ehler E. Sequential myofibrillar breakdown accompanies mitotic division of mammalian cardiomyocytes. J Cell Sci. 2004; 117: 3295-3306.
2. Alejandro Ocampo, et al. In Vivo Amelioration of Age-Associated Hallmarks by Partial Reprogramming Cell. 2016; 167:1719-1733.
3. Chen, C. Y., and Schwartz, R. J. Recruitment of the tinman homolog Nkx gene transcription (1996) Mol. Cell. Biol. 16, 6372-6384.
4. Del Re, D. P. et al. Yes-associated protein isoform 1 (Yap1) promotes cardiomyocyte survival and growth to protect against myocardial ischemic injury. J Biol Chem 288, 3977-3988 (2013).
5. Fan X, Hughes B G, Ali MAM, Cho W J, Lopez W, Schulz R. Dynamic Alterations to α-Actinin Accompanying Sarcomere Disassembly and Reassembly during Cardiomyocyte Mitosis. PLoS ONE 2015; 10: e0129176
6. Heallen T, Morikawa Y, Leach J, Tao G, Willerson J T, Johnson R L, Martin J F Hippo signaling impedes adult heart regeneration. Development. 2013; 140:4683-90.
7. Hill C S, Treisman R. Transcriptional regulation by extracellular signals: mechanisms and specificity. Cell 1995; 80:199-211.
8. Ikeda, S. & Sadoshima, J. Regulation of Myocardial Cell Growth and Death by the Hippo Pathway. Circ J 80, 1511-1519 (2016).
9. Karikó K, Buckstein M, Ni H, Weissman D. Suppression of RNA recognition by Toll-like receptors: the impact of nucleoside modification and the evolutionary origin of RNA Immunity. 2005; 23:165-75.
10. Karikó K1, Muramatsu H, Welsh F A, Ludwig J, Kato H, Akira S, Weissman D. Incorporation of pseudouridine into mRNA yields superior nonimmunogenic vector with increased translational capacity and biological stability. Mol Ther. 2008; 16:1833-40.
11. Krishnamurthy A, Villongco C T, Chuang J, Frank L R, Nigam V, Belezzuoli E, Stark P, Krummen D E, Narayan S, Omens J H, McCulloch A D, and Kerckhoffsa R C P, Patient-Specific Models of Cardiac Biomechanics J Comput Phys. 2013; 244: 4-21.
12. Leach J P, Heallen T, Zhang M, Rahmani M, Morikawa Y, Hill M C, Segura A, Willerson J T, Martin J F. Hippo pathway deficiency reverses systolic heart failure after infarction. Nature. 2017 Oct 4. doi: 10.1038/nature24045.
13. Li F, Wang X, Capasso J M, Gerdes A M. Rapid transition of cardiac myocytes from hyperplasia to hypertrophy during postnatal development. J Mol Cell Cardiol 1996; 28: 1737-1746.
14. Lockman K, Hinson J S, Medlin M D, Morris D, Taylor J M, Mack C P. Sphingosine 1-phosphate stimulates smooth muscle cell differentiation and proliferation by activating separate serum response factor co-factors. J Biol Chem 2004; 279:42422-42430.
15. Mahmoudi S, Brunet A Bursts of Reprogramming: A Path to Extend Lifespan? Cell. 2016; 167:1672-1674.
16. Mann D L, Bristow M R. Mechanisms and models in heart failure: the biomechanical model and beyond. Circulation. 2005; 111: 2837-49. Review.
17. Matsui, Y. et al. Lats2 is a negative regulator of myocyte size in the heart. Circ Res 103, 1309-1318 (2008).
18. McConnell, B. K., Popovic, Z., Mal, N., Lee, K., Bautista, J., Forudi, F., Schwartzman, R., Jin, J. P., Penn, M., and Bond, M. Disruption of protein kinase A interaction with A-kinase-anchoring proteins in the heart in vivo: effects on cardiac contractility, protein kinase A phosphorylation, and troponin I proteolysis. J Biol Chem, 2009; 284:1583-92.
19. Mercola, M., Ruiz-lozano, P. & Schneider, M. D. Cardiac muscle regeneration: lessons from development. Genes Dev. 2011; 25: 299-309.
20. Miano, J. S response factor: toggling between disparate programs of gene expression (2003) J. Mol. Cell. Cardiol. 35, 577-593.
21. Miralles F, Posern G, Zaromytidou A I, Treisman R. Actin dynamics control SRF activity by regulation of its coactivator MAL. Cell May 2 2003; 113(3):329-342.
22. Monroe, Tanner O., Hill, Matthew C., Morikawa, Y., Leach, John P., Heallen, Todd, Cao, Shuyi, Krijger, Peter H. L., Laat, Wouter de, Wehrens, Xander H. T., Rodney, George G., Martin, James F. YAP partially reprograms chromatin accessibility to directly induce adult cardiogenesis in vivo. Dev. Cell 2019; 48:765-779.
23. Niu Z, Iyer D, Conway S J, Martin J F, Ivey K, Srivastava D, Nordheim A, Schwartz R J. Serum response factor orchestrates nascent sarcomerogenesis and silences the biomineralization gene program in the heart. Proc Natl Acad Sci USA. 2008; 105:17824-17829.
24. Niu Z, Yu W, Zhang S X, Barron M, Belaguli N S, Schneider M D, Parmacek M, Nordheim A, Schwartz R J. Conditional mutagenesis of the murine serum response factor gene blocks cardiogenesis and the transcription of downstream gene targets. J Biol Chem. 2005; 280:32531-32538.
25. Percharde M, Lavial F, Ng J H, Kumar V, Tomaz R A, Martin N, Yeo J C, Gil J, Prabhakar S, Ng H H, Parker M G, Azuara V. Ncoa3 functions as an essential Esrrb coactivator to sustain embryonic stem cell self-renewal and reprogramming. Genes Dev. 2012; 26:2286-2298.
26. Reecy, J. M., Belaguli, N. S., and Schwartz, R. J. (1999) in Heart Development (Harvey, R., and Rosenthal, N., eds) pp. 273-290, Academic Press, New York.
27. Sanger J W, Wang J, Fan Y, White J, Sanger J M (2010) Assembly and dynamics of myofibrils. J Biomed. Biotechnol. 2010: 858606.
28. Sepulveda, J. L., Vlahopoulos, S., Iyer, D., Belaguli, N., and Schwartz, R. J. Combinatorial Expression of GATA4, Nkx2-5, and Serum Response Factor Directs Early Cardiac Gene Activity (2002) J. Biol. Chem. 277, 25775-25782.

29. Shah S J. Innovative Clinical Trial Designs for Precision Medicine in Heart Failure with Preserved Ejection Fraction. J Cardiovasc Transl Res. 2017 10:322-336.
30. Shore, P., and Sharrocks, A. D. The transcription factors Elk-1 and serum response factor interact by direct protein-protein contacts mediated by a short region of Elk-1 (1994) Mol. Cell. Biol. 14, 3283-3291.
31. Srivastava D, Olson E N. Knowing in your heart what's right. Trends Cell Biol 1997; 7: 447-453.
32. Treisman, R. Ternary complex factors: growth factor regulated transcriptional activators (1994) Curr. Opin. Genet. Dev. 4, 96-101.
33. Vartiainen M K, Guettler S, Larijani B, Treisman R. Nuclear actin regulates dynamic subcellular localization and activity of the SRF cofactor MAL. Science Jun. 22 2007; 316:1749-1752.
34. Wang, Z., Wang, D-Z., Hockemeyer, D., McAnally, J., Nordheim, A., and Olson, E. N. Myocardin and ternary complex factors compete for SRF to control smooth muscle gene expression (2004) Nature 428, 185-189.
35. Wang, D., Li, S., Hockemeyer, D., Sutherland, L., Schratt, G., Richardson, R. A., Nordheim, A., and Olson, E. N. Potentiation of serum response factor activity by a family of myocardin-related transcription factors. (2002) Proc. Natl. Acad. Sci. U.S.A 99, 14855-14860.
36. Xin M, Kim Y, Sutherland L B, Qi X, McAnally J, Schwartz R J, Richardson J A, Bassel-Duby R, Olson E N. Regulation of insulin-like growth factor signaling by Yap governs cardiomyocyte proliferation and embryonic heart size. Sci Signal. 2011; 4:ra70.
37. Xiao, Y., Leach, J., Wang, J. & Martin, J. F. Hippo/Yap Signaling in Cardiac Development and Regeneration. Curr Treat Options Cardiovasc Med 18, 38 (2016).
38. Yu O M, Miyamoto S, Brown J H. Myocardin-Related Transcription Factor A and Yes-Associated Protein Exert Dual Control in G Protein-Coupled Receptor- and RhoA-Mediated Transcriptional Regulation and Cell Proliferation. Mol Cell Biol. 2015; 36(1):39-49.
39. Zaromytidou A I, Miralles F, Treisman R M A L and ternary complex factor use different mechanisms to contact a common surface on the serum response factor DNA-binding domain. Mol Cell Biol. 2006; 2611:4134-4148
40. Zhao, B., Li, L., Tumaneng, K., Wang, C-Y., Guan, K.-L. A coordinated phosphorylation by Lats and CK1 regulates YAP stability through SCF (beta-TCRP). Genes Dev. 2010; 24:72-85.
41. Zhao, B., Wei, X., Li, W., Udan, R. S., Yang, Q., Kim, J., Xie, J., Ikenoue, T., Yu, J., Li, L., et al. Inactivation of YAP oncoprotein by the Hippo pathway is involved d in cell contact inhibition and tissue growth control. 2007; 21: 2747-2761.

What is claimed is:

1. A method of inducing cardiomyocyte regeneration comprising:
   a) preparing a first modified messenger RNA for expressing a mutated serum response factor polypeptide SRF-153(A3);
   b) preparing a second modified messenger RNA for expressing a mutated YAP polypeptide; and
   c) delivering the first and second modified messenger RNAs using a lipid nanoparticle into a heart tissue of a subject.

2. The method of claim 1, wherein a damaged area of the heart tissue is identified and the first and second modified messenger RNAs are delivered into a site adjacent the damaged area.

3. The method of claim 2, wherein the mutated YAP polypeptide is YAP1(5SA).

4. The method of claim 3, wherein the heart tissue that the first and second modified messenger RNAs are injected into exhibit upregulation of multiple cell cycle gene clusters.

5. A method for promoting cardiac repair and regeneration in a subject, the method comprising injecting an effective amount of a therapeutic composition into a site of a heart tissue of the subject, wherein the composition comprises a first modified messenger RNA for expressing a mutated serum response factor polypeptide SRF-153(A3), a second modified messenger RNA for expressing a mutated YAP polypeptide, and a lipid nanoparticle for delivering the first and second modified messenger RNAs into the heart tissue.

6. The method of claim 5, wherein the site of the injection is adjacent to an identified site of cardiac damage.

7. The method of claim 6, wherein one or more sites of cardiac damage is identified using echocardiography or ultrasound.

8. The method of claim 5, wherein the mutated YAP polypeptide is YAP1(5SA).

9. The method of claim 7, wherein the therapeutic composition is injected in one or more border areas between visualized healthy and damaged heart tissue.

10. The method of claim 7, wherein thetherapeutic composition is injected within two weeks of a diagnosis of heart tissue damage.

11. The method of claim 6, wherein the repair and regeneration of the heart tissue at the site of the injection is assessed using echocardiograms.

12. The method of claim 9, wherein the therapeutic composition is injected at multiple sites using a cardiac catheter.

13. The method of claim 9, wherein the method is used to treat a myocardial infarction.

14. A method for promoting cardiac repair and regeneration in a subject, the method comprising identifying a site of cardiac muscle damage in a heart of the subject and injecting a therapeutic composition containing both a messenger RNA for SRF-153(A3) and YAP1(5SA) into an injection site in the heart adjacent the site of cardiac muscle damage.

15. The method of claim 14, wherein multiple injections of the therapeutic composition are made at different locations in the heart.

16. The method of claim 14, wherein multiple sites of cardiac muscle damage are identified in the heart.

17. The method of claim 16, wherein multiple injections of the therapeutic composition are made at different locations in the heart and wherein each injection location is adjacent to one of the identified sites of cardiac damage.

18. The method of claim 14, wherein the therapeutic composition comprises lipid nanoparticle for delivering the first and second modified messenger RNAs the heart.

19. The method of claim 18, wherein the subject has suffered a myocardial infarction.

20. The method of claim 17, wherein one or more locations of cardiac damage is identified using echocardiography or ultrasound.

21. The method of claim 19, wherein the therapeutic composition is injected within two weeks of a diagnosis of myocardial infarction.

22. The method of claim 21, wherein the repair and regeneration of the heart tissue at the site of the injection is assessed using echocardiograms.

\* \* \* \* \*

SEQUENCE LISTING

```
<160> NUMBER OF SEQ ID NOS: 13

<210> SEQ ID NO 1
<211> LENGTH: 508
<212> TYPE: PRT
<213> ORGANISM: Artificial Sequence
<220> FEATURE:
<223> OTHER INFORMATION: Human Serum Response Factor

<400> SEQUENCE: 1

Met Leu Pro Thr Gln Ala Gly Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
        35                  40                  45

Ala Gly Leu Gly Pro Gly Arg Leu Glu Arg Glu Ala Ala Ala Ala
    50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Glu Leu Gly Ala Glu Arg Arg
                85                  90                  95

Gly Leu Lys Arg Ser Leu Ser Glu Met Glu Ile Gly Met Val Val Gly
            100                 105                 110

Gly Pro Glu Ala Ser Ala Ala Ala Thr Gly Gly Tyr Gly Pro Val Ser
        115                 120                 125

Gly Ala Val Ser Gly Ala Lys Pro Gly Lys Lys Thr Arg Gly Arg Val
    130                 135                 140

Lys Ile Lys Met Glu Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175
```

```
Thr Leu Thr Gly Thr Gln Val Leu Leu Val Ala Ser Glu Thr Gly
            180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
            260                 265                 270

Pro Gly Thr Thr Ser Thr Ile Gln Thr Ala Pro Ser Thr Ser Thr Thr
        275                 280                 285

Met Gln Val Ser Ser Gly Pro Ser Phe Pro Ile Thr Asn Tyr Leu Ala
    290                 295                 300

Pro Val Ser Ala Ser Val Ser Pro Ser Ala Val Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
        355                 360                 365

Ala Ser Pro Ser Arg Asp Ser Ser Thr Asp Leu Thr Gln Thr Ser Ser
    370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
            420                 425                 430

Ala Phe Ser Gln Ala Pro Ser Thr Met Gln Val Ser His Ser Gln Val
        435                 440                 445

Gln Glu Pro Gly Gly Val Pro Gln Val Phe Leu Thr Ala Ser Ser Gly
    450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
            500                 505

<210> SEQ ID NO 2
<211> LENGTH: 508
<212> TYPE: PRT
<213> ORGANISM: Artificial Sequence
<220> FEATURE:
<223> OTHER INFORMATION: Synthetic polypeptide

<400> SEQUENCE: 2

Met Leu Pro Thr Gln Ala Gly Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30
```

```
Gly Gly Gly Thr Arg Gly Ala Asn Gly Gly Arg Val Pro Gly Asn Gly
            35                  40                  45

Ala Gly Leu Gly Pro Gly Arg Leu Glu Arg Glu Ala Ala Ala Ala Ala
 50                  55                  60

Ala Thr Thr Pro Ala Pro Thr Ala Gly Ala Leu Tyr Ser Gly Ser Glu
 65                  70                  75                  80

Gly Asp Ser Glu Ser Gly Glu Glu Glu Leu Gly Ala Glu Arg Arg
                85                  90                  95

Gly Leu Lys Arg Ser Leu Ser Glu Met Glu Ile Gly Met Val Val Gly
                100                 105                 110

Gly Pro Glu Ala Ser Ala Ala Ala Thr Gly Gly Tyr Gly Pro Val Ser
            115                 120                 125

Gly Ala Val Ser Gly Ala Lys Pro Gly Lys Lys Thr Arg Gly Arg Val
130                 135                 140

Lys Ile Lys Met Glu Phe Ile Asp Ala Ala Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
                180                 185                 190

His Val Tyr Thr Phe Ala Thr Arg Lys Leu Gln Pro Met Ile Thr Ser
            195                 200                 205

Glu Thr Gly Lys Ala Leu Ile Gln Thr Cys Leu Asn Ser Pro Asp Ser
            210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
                260                 265                 270

Pro Gly Thr Thr Ser Thr Ile Gln Thr Ala Pro Ser Thr Ser Thr Thr
            275                 280                 285

Met Gln Val Ser Ser Gly Pro Ser Phe Pro Ile Thr Asn Tyr Leu Ala
290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
            355                 360                 365

Ala Ser Pro Ser Arg Asp Ser Ser Thr Asp Leu Thr Gln Thr Ser Ser
            370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
                420                 425                 430

Ala Phe Ser Gln Ala Pro Ser Thr Met Gln Val Ser His Ser Gln Val
            435                 440                 445

Gln Glu Pro Gly Gly Val Pro Gln Val Phe Leu Thr Ala Ser Ser Gly
```

```
            450                 455                 460
Thr Val Gln Ile Pro Val Ser Ala Val Gln Leu His Gln Met Ala Val
465                 470                 475                 480

Ile Gly Gln Gln Ala Gly Ser Ser Asn Leu Thr Glu Leu Gln Val
                485                 490                 495

Val Asn Leu Asp Thr Ala His Ser Thr Lys Ser Glu
            500                 505
```

<210> SEQ ID NO 3
<211> LENGTH: 508
<212> TYPE: PRT
<213> ORGANISM: Artificial Sequence
<220> FEATURE:
<223> OTHER INFORMATION: Synthetic Polypeptide

<400> SEQUENCE: 3

```
Met Leu Pro Thr Gln Ala Gly Ala Ala Ala Leu Gly Arg Gly Ser
1               5                   10                  15

Ala Leu Gly Gly Ser Leu Asn Arg Thr Pro Thr Gly Arg Pro Gly Gly
                20                  25                  30

Gly Gly Gly Thr Arg Gly Ala Asn Gly Gly Arg Val Pro Gly Asn Gly
            35                  40                  45

Ala Gly Leu Gly Pro Gly Arg Leu Glu Arg Glu Ala Ala Ala Ala
50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Leu Gly Ala Glu Arg Arg
                85                  90                  95

Gly Leu Lys Arg Ser Leu Ser Glu Met Glu Ile Gly Met Val Val Gly
                100                 105                 110

Gly Pro Glu Ala Ser Ala Ala Ala Thr Gly Gly Tyr Gly Pro Val Ser
            115                 120                 125

Gly Ala Val Ser Gly Ala Lys Pro Gly Lys Lys Thr Arg Gly Arg Val
        130                 135                 140

Lys Ile Ala Ala Ala Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
                180                 185                 190

His Val Tyr Thr Phe Ala Thr Arg Lys Leu Gln Pro Met Ile Thr Ser
            195                 200                 205

Glu Thr Gly Lys Ala Leu Ile Gln Thr Cys Leu Asn Ser Pro Asp Ser
        210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
                260                 265                 270

Pro Gly Thr Thr Ser Thr Ile Gln Thr Ala Pro Ser Thr Ser Thr Thr
            275                 280                 285

Met Gln Val Ser Ser Gly Pro Ser Phe Pro Ile Thr Asn Tyr Leu Ala
        290                 295                 300

Pro Val Ser Ala Ser Val Ser Pro Ser Ala Val Ser Ser Ala Asn Gly
```

```
                    305                 310                 315                 320
Thr Val Leu Lys Ser Thr Gly Ser Gly Pro Val Ser Ser Gly Gly Leu
                325                 330                 335
Met Gln Leu Pro Thr Ser Phe Thr Leu Met Pro Gly Gly Ala Val Ala
                340                 345                 350
Gln Gln Val Pro Val Gln Ala Ile Gln Val His Gln Ala Pro Gln Gln
                355                 360                 365
Ala Ser Pro Ser Arg Asp Ser Ser Thr Asp Leu Thr Gln Thr Ser Ser
                370                 375                 380
Ser Gly Thr Val Thr Leu Pro Ala Thr Ile Met Thr Ser Ser Val Pro
385                 390                 395                 400
Thr Thr Val Gly Gly His Met Met Tyr Pro Ser Pro His Ala Val Met
                405                 410                 415
Tyr Ala Pro Thr Ser Gly Leu Gly Asp Gly Ser Leu Thr Val Leu Asn
                420                 425                 430
Ala Phe Ser Gln Ala Pro Ser Thr Met Gln Val Ser His Ser Gln Val
                435                 440                 445
Gln Glu Pro Gly Gly Val Pro Gln Val Phe Leu Thr Ala Ser Ser Gly
                450                 455                 460
Thr Val Gln Ile Pro Val Ser Ala Val Gln Leu His Gln Met Ala Val
465                 470                 475                 480
Ile Gly Gln Gln Ala Gly Ser Ser Ser Asn Leu Thr Glu Leu Gln Val
                485                 490                 495
Val Asn Leu Asp Thr Ala His Ser Thr Lys Ser Glu
                500                 505

<210> SEQ ID NO 4
<211> LENGTH: 93
<212> TYPE: PRT
<213> ORGANISM: Artificial Sequence
<220> FEATURE:
<223> OTHER INFORMATION: Synthetic Polypeptide

<400> SEQUENCE: 4

Ser Gly Ala Lys Pro Gly Lys Lys Thr Arg Gly Arg Val Lys Ile Lys
1               5                   10                  15
Met Glu Phe Ile Asp Asn Lys Leu Arg Arg Tyr Thr Thr Phe Ser Lys
                20                  25                  30
Arg Lys Thr Gly Ile Met Lys Lys Ala Tyr Glu Leu Ser Thr Leu Thr
            35                  40                  45
Gly Thr Gln Val Leu Leu Leu Val Ala Ser Glu Thr Gly His Val Tyr
        50                  55                  60
Thr Phe Ala Thr Arg Lys Leu Gln Pro Met Ile Thr Ser Glu Thr Gly
65                  70                  75                  80
Lys Ala Leu Ile Gln Thr Cys Leu Asn Ser Pro Asp Ser
                85                  90

<210> SEQ ID NO 5
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 5

Ser Gly Ala Lys Pro Gly Lys Lys Thr Arg Gly Arg Val Lys Ile Lys
1               5                   10                  15
```

Met Glu Phe Ile Asp Asn Lys Leu Arg Arg Tyr Thr Thr Phe Ser Lys
            20                  25                  30

Arg Lys Thr Gly Ile Met Lys Lys Ala Tyr Glu Leu Ser Thr Leu Thr
        35                  40                  45

<210> SEQ ID NO 6
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 6

Ser Gly Ala Lys Pro Gly Lys Lys Thr Arg Gly Arg Val Lys Ile Lys
1               5                   10                  15

Met Glu Phe Ile Asp Ala Ala Ala Arg Arg Tyr Thr Thr Phe Ser Lys
            20                  25                  30

Arg Lys Thr Gly Ile Met Lys Lys Ala Tyr Glu Leu Ser Thr Leu Thr
        35                  40                  45

<210> SEQ ID NO 7
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 7

Ser Gly Ala Lys Pro Gly Lys Lys Thr Arg Gly Arg Val Lys Ile Ala
1               5                   10                  15

Ala Ala Phe Ile Asp Asn Lys Leu Arg Arg Tyr Thr Thr Phe Ser Lys
            20                  25                  30

Arg Lys Thr Gly Ile Met Lys Lys Ala Tyr Glu Leu Ser Thr Leu Thr
        35                  40                  45

<210> SEQ ID NO 8
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 8

Ser Gly Ala Lys Pro Gly Lys Lys Thr Ala Ala Ala Val Lys Ile Lys
1               5                   10                  15

Met Glu Phe Ile Asp Asn Lys Leu Arg Arg Tyr Thr Thr Phe Ser Lys
            20                  25                  30

Arg Lys Thr Gly Ile Met Lys Lys Ala Tyr Glu Leu Ser Thr Leu Thr
        35                  40                  45

<210> SEQ ID NO 9
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 9

Ser Gly Ala Lys Pro Gly Lys Lys Thr Arg Gly Arg Ala Ala Ala Lys
1               5                   10                  15

Met Glu Phe Ile Asp Asn Lys Leu Arg Arg Tyr Thr Thr Phe Ser Lys
            20                  25                  30

Arg Lys Thr Gly Ile Met Lys Lys Ala Tyr Glu Leu Ser Thr Leu Thr
            35                  40                  45

<210> SEQ ID NO 10
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 10

Ser Gly Ala Lys Pro Gly Lys Lys Thr Arg Gly Arg Val Lys Ile Lys
1               5                   10                  15

Met Glu Ala Ala Ala Asn Lys Leu Arg Arg Tyr Thr Thr Phe Ser Lys
            20                  25                  30

Arg Lys Thr Gly Ile Met Lys Lys Ala Tyr Glu Leu Ser Thr Leu Thr
            35                  40                  45

<210> SEQ ID NO 11
<211> LENGTH: 1526
<212> TYPE: RNA
<213> ORGANISM: Artificial Sequence
<220> FEATURE:
<223> OTHER INFORMATION: mRNA for Serum Response Factor

<400> SEQUENCE: 11
auguuaccga cccaagcugg ggccgcggcg gcucugggcc ggggcucggc ccuggggggc      60
agccugaacc ggaccccgac ggggcggccg ggcggcggcg gcgggacacg cggggcuaac    120
gggggccggg uccccgggaa uggcgcgggg cucgggcccg ccgccugga gcgggaggcu     180 gcggcagcgg cggcaaccac cccggcgccc accgcggggg cccucuacag cggcagcgag    240
ggcgacucga gucgggcga ggaggaggag cuggcgccg agcggcgcgg ccugaagcgg      300
agccugagcg agauggagau cgguauggug gucgguggc ccgaggcguc ggcagcggcc     360
accgggggcu acgggccggu gagcggcgcg gugagcgggg ccaagccggg uaagaagacc    420
cggggccgcg ugaagaucaa gauggaguuc aucgacaaca agcugcggcg cuacacgacc    480
uucagcaaga ggaagacggg caucaugaag aaggccuaug agcugccac gcugacaggg     540 acacaggugc uguugcuggu ggccagugag acaggccaug uguauaccuu ugccacccga    600
aaacugcagc ccaugaucac cagugagacc ggcaaggcac ugauucagac cgccucaac    660 ucgccagacu cuccaccccg uucagacccc acaacagacc agagaaugag ugccacuggc    720
uuugaagaga cagaucucac cuaccaggug ucggagucug acagcagugg ggagaccaag    780
gacacacuga agccggcguu cacagucacc aaccugccgg guacaaccuc caccauccaa    840
acagcaccua gcaccucuac caccaugcaa gucagcagcg gccccuccuu ucccaucacc    900
aacuaccugg caccagcuc ugcuaguguc agccccagug cugucagcag ugccaauggg    960
acugugcuga gaguacagg cagcggcccu gucuccucug ggggccuuau gcagcugccu   1020
accagcuuca cccucaugcc ugguggggca guggcccagc agguccccagu gcaggccauu   1080 caagugcacc aggccccaca gcaagcgucu cccucccgug acagcagcac agaccucacg   1140
cagaccuccu ccagcgggac agugacgcug ccgccacca ucaugacguc auccgugccc   1200
acaacugugg guggccacau gauguacccu agcccgcaug cggugaugua ugccccccac   1260
ucgggccugg gugauggcag ccucaccgug cugaaugccu ucucccaggc accauccacc   1320
augcaggugu cacacagcca gguccaggag ccagguggcg uccccagggg uuccugacag   1380
caucaucugg gacagugcag aucccuguuu cagcaguuca gcuccaccag auggcuguga   1440

| | |
|---|---|
| uagggcagca ggccgggagc agcagcaacc ucaccgagcu acaggggugug aaccuggaca | 1500 |
| ccgcccacag caccaagagu gaauga | 1526 |

<210> SEQ ID NO 12
<211> LENGTH: 1526
<212> TYPE: RNA
<213> ORGANISM: Artificial Sequence
<220> FEATURE:
<223> OTHER INFORMATION: Synthetic mRNA

<400> SEQUENCE: 12

| | |
|---|---|
| auguuaccga cccaagcugg ggccgcggcg gcucugggcc ggggcucggc ccugggggc | 60 |
| agccugaacc ggaccccgac ggggcggccg ggcggcggcg gcgggacacg cggggcuaac | 120 |
| gggggccggg uccccgggaa uggcgcgggg cucgggcccg gccgccugga gcggaggcu | 180 |
| gcggcagcgg cggcaaccac cccggcgccc accgcggggg cccucuacag cggcagcgag | 240 |
| ggcgacucgg agucgggcga ggaggaggag cuggcgcccg agcggcgcgg ccugaagcgg | 300 |
| agccugagcg agauggagau cgguaugugu gucggugggc ccgaggcguc ggcagcggcc | 360 |
| accgggggcu acgggccggu gagcggcgcg gugagcgggg ccaagccggg uaagaagacc | 420 |
| cggggccgcg ugaagaucaa gauggaguuc aucgaccgac gacgacggcg cuacacgacc | 480 |
| uucagcaaga ggaagacggg caucaugaag aaggccuaug agcugccacc gcugacaggg | 540 |
| acacaggugc uguugcuggu ggccagugag acaggccaug uguauaccuu ugccacccga | 600 |
| aaacugcagc ccaugaucac caguggagacc ggcaaggcac ugauucagac cugccucaac | 660 |
| ucgccagacu cuccaccccg uucagacccc acaacagacc agagaaugag ugccacuggc | 720 |
| uuugaagaga cagaucucac cuaccaggug ucggagucug acagcagugg ggagaccaag | 780 |
| gacacacuga agccggcguu cacagucacc aaccugccgg guacaaccuc caccauccaa | 840 |
| acagcaccua gcaccucuac caccaugcaa gucagcagcg gccccuccuu ucccaucacc | 900 |
| aacuaccugg caccagguguc ugcuagugu c agccccagug cugucagcag ugccaauggg | 960 |
| acugugcuga gaguacagg cagcggcccu gucuccucug ggggccuuau gcagcugccu | 1020 |
| accagcuuca cccucaugcc uggugggca guggcccagc aggucccagu gcaggccauu | 1080 |
| caagugcacc aggccccaca gcaagcgucu cccucccgug acagcagcac agaccucacg | 1140 |
| cagaccuccu ccagcgggac agugacgcug cccgccacca ucaugacguc auccgugccc | 1200 |
| acaacugugg guggccacau gauguacccu agcccgcaug cggugaugua ugccccccacc | 1260 |
| ucgggccugg gugauggcag ccucaccgug cugaaugccu cucccaggc accauccacc | 1320 |
| augcaggugu cacacagcca gguccaggag ccagguggcg ucccccaggg uuccugacag | 1380 |
| caucaucugg gacagugcag aucccuguuu cagcaguuca gcccaccag auggcuguga | 1440 |
| uagggcagca ggccgggagc agcagcaacc ucaccgagcu acaggggugug aaccuggaca | 1500 |
| ccgcccacag caccaagagu gaauga | 1526 |

<210> SEQ ID NO 13
<211> LENGTH: 1636
<212> TYPE: RNA
<213> ORGANISM: Artificial Sequence
<220> FEATURE:
<223> OTHER INFORMATION: mRNA for YAP1

<400> SEQUENCE: 13

| | |
|---|---|
| auggauccccg ggcagcagcc gccgccucaa ccggcccccc agggccaagg gcagccgccu | 60 |

```
ucgcagcccc cgcaggggca gggcccgccg uccggacccg ggcaaccggc acccgcggcg      120
acccaggcgg cgccgcaggc acccccgcc gggcaucaga ucgugcacgu ccgcggggac      180
ucggagaccg accuggaggc gcucuucaac gccgucauga accccaagac ggccaacgug      240
ccccagaccg ugcccaugag gcuccggaag cugcccguau cccuucuuca agccgccgga      300
gcccaaaucc cacucccgac aggccaguac ugaugcaggc acugcaggag cccugacucc      360
cagcauguuc gagcucauuc cucuccagcu ucucugcagu ugggagcugu uucuccuggg      420 auggacccg ggcagcagcc gccgccucaa ccggccccc agggccaagg gcagccgccu       480
ucgcagcccc cgcaggggca gggcccgccg uccggacccg ggcaaccggc acccgcggcg      540
acacugaccc ccacuggagu agucucuggc ccagcagcua cacccacagc ucagcaucuu      600
cgacagucuu cuuuugagaa uaccugauga uguaccucug ccagcgguug ggagauggca      660
aagacaucuu cuggucagag auacuucuua aaucacaucg aucagacaac aacauggcag      720
gaccccagga aggccaugcu gucccagaug aacgucacag cccccaccag uccaccagug      780
cagcagaaua ugaugaacuc ggcuucaggu ccucuuccug auggauggga acaagccaug      840
acucaggaug gagaaauuua cuauauaaac cauaagaaca agaccaccuc uuggcuagac      900
ccaaggcuug acccucguuu ugccaugaac cagagaauca gucagagugc uccagugaaa      960
cagccaccac cccuggcucc ccagagccca cagggaggcg ucauggguqq cagcaacucc     1020 aaccagcagc aacagaugcg acugcagcaa cugcagaugu agaaggagag gcugcggcug     1080
aaacagcaag aacugcuucg gcaggcaaug cggaauauca aucccagcac agcaaauucu     1140
ccaaaauguc aggaguuagc ccugcguagc caguuaccaa cacuggagca ggauggggg      1200 acucaaaauc caguguuc ucccgggaug ucucaggaau ugagaacaau gacgaccaau      1260
agcucagauc cuuccuuaa caguggcacc uaucacucuc gagaugagag uacagacagu     1320
gggacuaagc augagcagcu acaguguccc ucgaaccccg gaugacuucc ugaacagugu     1380
ggaugagaug gauacaggug auacuaucaa ccaaagcacc cugcccucac agcagaaccg     1440
uuucccagac uaccuugaag ccauuccugg gacaaaugug gaccuuggaa cacuggaagg     1500
agauggaaug aacauagaag gagaggagcu gaugccaagu cugcaggaag cuuugaguuc     1560
ugacauccuu aaugacaugg agucuguuuu ggcugccacc aagcuagaua aagaaagcuu     1620
ucuuacaugg uuauag                                                     1636
```